United States Patent [19]
North et al.

[11] Patent Number: 5,776,762
[45] Date of Patent: Jul. 7, 1998

[54] OBESITY ASSOCIATED GENES

[75] Inventors: Michael North, La Jolla, Calif.; Patsy Nishina, Bar Harbor, Me.; Konrad Noben-Trauth, Bar Harbor, Me.; Juergen Naggert, Bar Harbor, Me.

[73] Assignees: Sequana Therapeutics, Inc., La Jolla, Calif.; The Jackson Laboratory, Bar Harbor, Me.

[21] Appl. No.: 714,991

[22] Filed: Sep. 17, 1996

Related U.S. Application Data

[63] Continuation-in-part of Ser. No. 630,592, Apr. 10, 1996.

[51] Int. Cl.$^6$ .................... C07H 21/04; C12Q 1/68; C12N 15/70; C12N 15/74
[52] U.S. Cl. .................... 435/252.3; 435/6; 435/69.1; 435/172.3; 435/325; 536/23.1; 536/24.3; 536/24.31; 536/23.5
[58] Field of Search .................... 536/23.1, 23.5, 536/24.3, 24.31; 435/6, 172.3, 69.1, 325, 252.3

[56] References Cited

U.S. PATENT DOCUMENTS 5,646,040  7/1997  Kleyn et al. .................... 435/325

OTHER PUBLICATIONS

GenBank sequence, accession number X69827.
Noben–Trauth et al. (1996) *Nature* 380:534–538.
Kleyn et al. (1996) *Cell* 65:281–290.
Heckenlively et al. (1995) *P.N.A.S.* 92:11100–11104.
Lee et al. (1996) *Nature* 379:632–635.
Ohlemiller et al. (1995) *Neuroreport* 6:845–9.
Samuelson et al. (1995) *Genome* 6:242–6.
Zhang et al. (1994) *Nature* 372:425–432.
Nishina et al. (1994) *Metabolism* 43:549–553.
Jones et al. (1992) *Genomics* 14:197–9.
Coleman and Eicher (1990) *J Hered* 81:424–7.

*Primary Examiner*—Jasemine C. Chambers
*Assistant Examiner*—Scott D. Priebe
*Attorney, Agent, or Firm*—Pamela J. Sherwood; Bozicevic & Reed LLP

[57] ABSTRACT

The gene responsible for the autosomal recessive mouse obesity mutation tub was identified by positional cloning. The homologous human gene is also provided. The genes are used to produce tubby protein; in screening for compositions that modulate the expression or function of the tubby protein; and in studying associated physiological pathways. The DNA is further used as a diagnostic for genetic predisposition to obesity, retinal degeneration or cochlear degeneration. The mutation responsible for the tub phenotype is a G to T transversion that abolishes a donor splice site in the 3' coding region and results in a larger transcript containing the unspliced intron. A second, prematurely truncated transcript arises from the introduction of a premature polyadenylation site in the unspliced intron.

4 Claims, 1 Drawing Sheet ns are able to permanently achieve significant weight loss.

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
        ( A ) LENGTH: 2119 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

```
ATCAGCCCAA  GATGGAGGCA  GGCTAGTTTA  TCACTACCTG  TATCTTATCT  GCTAGCCAAT      60
GGTACTAAAA  CCTATGGCTC  AGTGTCCCTC  TTCCCAACCA  GGAAATGTGG  AAGACAGTGG     120
GAAAGGAAGG  ACCGTGCTCG  TGGAAAACAG  CCTCTGACCC  CAGACACAAC  TGTATGGAAA     180
GTCCAGGGCT  GTGTGACAGT  TCCTGTGACA  GGAAAACACC  TCCCCGTGTG  CACCAGGCA      240
GTGAGATGTC  CCTAGACATT  TTCATTGGCA  CCGAGGAAGG  CATGTTCTTT  GGTATGCTTA     300
GCCGAGACCA  ACACCTGGAA  TGATACCAGG  TGGCTGCCTC  TGACCCCAAC  ACTGTGCTTG     360
GAAAGAATGT  AGCCTGTGAC  TTCTAGTAAA  AGTGTCCTAG  ATGATGAGGG  CAGCAACCTG     420
AGGCAGCAGA  AGCTCGACCG  GCAGCGGGCC  CTGTTGGAAC  AGAAGCAGAA  GAAGAAGCGC     480
CAAGAGCCCT  TGATGGTACA  GGCCAATGCA  GATGGACGGC  CCCGGAGTCG  GCGAGCCCGG     540
CAGTCAGAGG  AGCAAGCCCC  CCTGGTGGAG  TCCTACCTCA  GCAGCAGTGG  CAGCACCAGC     600
TACCAAGTTC  AAGAGGCCGA  CTCGATTGCC  AGTGTACAGC  TGGGAGCCAC  CCGCCCACCA     660
GCACCAGCCT  CAGCCAAGAA  ATCCAAGGGA  GCGGCTGCAT  CTGGGGCCA   GGTGGAGCC      720
CCTAGGAAGG  AGAAGAAGGG  AAAGCATAAA  GGCACCAGCG  GGCCAGCAAC  TCTGGCAGAA     780
GACAAGTCTG  AGGCCCAAGG  CCCAGTGCAG  ATCTTGACTG  TGGGACAGTC  AGACCACGAC     840
AAGGATGCGG  GAGAGACAGC  AGCCGGCGGG  GGCGCACAGC  CCAGTGGGCA  GGACCTCCGT     900
GCCACGATGC  AGAGGAAGGG  CATCTCCAGC  AGCATGAGCT  TGACGAGGA   CGAGGATGAG     960
GATGAAAACA  GCTCCAGCTC  CTCCCAGCTA  AACAGCAACA  CCCGCCCTAG  TTCTGCCACT    1020
AGCAGAAAGT  CCATCCGGGA  GGCAGCTTCA  GCCCCCAGCC  CAGCCGCCCC  AGAGCCACCA    1080
GTGGATATTG  AGGTCCAGGA  TCTAGAGGAG  TTTGCACTGA  GGCCAGCCCC  ACAAGGGATC    1140
ACCATCAAAT  GCCGCATCAC  TCGGGACAAG  AAGGGGATGG  ACCGCGGCAT  GTACCCCACC    1200
TACTTTCTGC  ACCTAGACCG  TGAGGATGGC  AAGAAGGTGT  TCCTCCTGGC  GGGCAGGAAG    1260
AGAAAGAAGA  GTAAAACTTC  CAATTACCTC  ATCTCTGTGG  ACCCAACAGA  CTTGTCTCGG    1320
GGAGGCGATA  GCTATATCGG  GAAGTTGCGG  TCCAACCTGA  TGGGCACCAA  GTTCACCGTT    1380
TATGACAATG  GCGTCAACCC  TCAGAAGGCA  TCCTCTTCCA  CGCTGGAAAG  CGGAACCTTG    1440
CGCCAGGAGC  TGGCAGCGGT  GTGCTATGAG  ACAAATGTCC  TAGGCTTCAA  GGGACCTCGG    1500
AAGATGAGTG  TGATCGTCCC  AGGCATGAAC  ATGGTTCATG  AGAGAGTCTG  TATCCGCCCC    1560
CGCAATGAAC  ATGAGACCCT  GTTAGCACGC  TGGCAGAACA  AGAACACGGA  GAGCATCATT    1620
GAGCTGCAGA  ACAAGACGCC  AGTCTGGAAT  GATGACACAC  AGTCCTATGT  ACTTAACTTC    1680
CACGGCCGTG  TCACACAGGC  TTCTGTGAAG  AACTTCCAGA  TCATCCACGG  CAATGACCCG    1740
GACTACATCG  TCATGCAGTT  TGGCCGGGTA  GCAGAAGATG  TGTTCACCAT  GGATTACAAC    1800
TACCCACTGT  GTGCACTGCA  GGCCTTTGCC  ATTGCTCTGT  CCAGCTTTGA  CAGCAAGCTG    1860
GCCTGCGAGT  AGAGGCCCCC  ACTGCCTTTA  GGTGGCCCAG  TCCGGAGTGG  AGCTTGCCTG    1920
CCTGCCAAGA  CAGCCCTGCC  TACCCTCTGT  TCATAGGCCC  TCTATGGGCT  TTCTGGCCTT    1980
ACCAACCAGA  GACTGGCTGC  TCTGCCTCTG  CTGCTGAAGC  AGGGGGGACA  GCAAATGGGT    2040
```

| | | | | | | | | | | | | | | |
|---|---|---|---|---|---|---|---|---|---|---|---|---|---|---|
ATGACAGGAG AAGAATATTT CTGTGCCCCA AGGTCAACAA CACACATGCC CAGTCCTGGA     2100

AAAAAAAAAA AAAAAAAA     2119

( 2 ) INFORMATION FOR SEQ ID NO:2:

( i ) SEQUENCE CHARACTERISTICS:
        ( A ) LENGTH: 459 amino acids
        ( B ) TYPE: amino acid
        ( C ) STRANDEDNESS: double
        ( D ) TOPOLOGY: linear ( i i ) MOLECULE TYPE: peptide ( x i ) SEQUENCE DESCRIPTION: SEQ ID NO:2:

```
Met Val Gln Ala Asn Ala Asp Gly Arg Pro Arg Ser Arg Arg Ala Arg
 1               5                  10                  15

Gln Ser Glu Glu Gln Ala Pro Leu Val Glu Ser Tyr Leu Ser Ser Ser
             20                  25                  30

Gly Ser Thr Ser Tyr Gln Val Gln Glu Ala Asp Ser Ile Ala Ser Val
         35                  40                  45

Gln Leu Gly Ala Thr Arg Pro Pro Ala Pro Ala Ser Ala Lys Lys Ser
     50                  55                  60

Lys Gly Ala Ala Ala Ser Gly Gln Gly Gly Ala Pro Arg Lys Glu
 65                  70                  75                  80

Lys Lys Gly Lys His Lys Gly Thr Ser Gly Pro Ala Thr Leu Ala Glu
                 85                  90                  95

Asp Lys Ser Glu Ala Gln Gly Pro Val Gln Ile Leu Thr Val Gly Gln
                100                 105                 110

Ser Asp His Asp Lys Asp Ala Gly Glu Thr Ala Ala Gly Gly Gly Ala
            115                 120                 125

Gln Pro Ser Gly Gln Asp Leu Arg Ala Thr Met Gln Arg Lys Gly Ile
    130                 135                 140

Ser Ser Ser Met Ser Phe Asp Glu Asp Glu Asp Glu Asp Glu Asn Ser
145                 150                 155                 160

Ser Ser Ser Ser Gln Leu Asn Ser Asn Thr Arg Pro Ser Ser Ala Thr
                165                 170                 175

Ser Arg Lys Ser Ile Arg Glu Ala Ala Ser Ala Pro Ser Pro Ala Ala
            180                 185                 190

Pro Glu Pro Pro Val Asp Ile Glu Val Gln Asp Leu Glu Glu Phe Ala
    195                 200                 205

Leu Arg Pro Ala Pro Gln Gly Ile Thr Ile Lys Cys Arg Ile Thr Arg
210                 215                 220

Asp Lys Lys Gly Met Asp Arg Gly Met Tyr Pro Thr Tyr Phe Leu His
225                 230                 235                 240

Leu Asp Arg Glu Asp Gly Lys Lys Val Phe Leu Leu Ala Gly Arg Lys
                245                 250                 255

Arg Lys Lys Ser Lys Thr Ser Asn Tyr Leu Ile Ser Val Asp Pro Thr
            260                 265                 270

Asp Leu Ser Arg Gly Gly Asp Ser Tyr Ile Gly Lys Leu Arg Ser Asn
    275                 280                 285

Leu Met Gly Thr Lys Phe Thr Val Tyr Asp Asn Gly Val Asn Pro Gln
290                 295                 300

Lys Ala Ser Ser Ser Thr Leu Glu Ser Gly Thr Leu Arg Gln Glu Leu
305                 310                 315                 320

Ala Ala Val Cys Tyr Glu Thr Asn Val Leu Gly Phe Lys Gly Pro Arg
                325                 330                 335
```

|       |     |     |     |       |     |     |     |     |     |     |     |       |     |     |
|-------|-----|-----|-----|-------|-----|-----|-----|-----|-----|-----|-----|-------|-----|-----|
| Lys   | Met | Ser | Val | Ile   | Val | Pro | Gly | Met | Asn | Met | Val | His   | Glu | Arg | Val |
|       |     |     | 340 |       |     |     | 345 |     |     |     |     | 350   |     |     |
| Cys   | Ile | Arg | Pro | Arg   | Asn | Glu | His | Glu | Thr | Leu | Leu | Ala   | Arg | Trp | Gln |
|       |     | 355 |     |       |     |     | 360 |     |     |     |     | 365   |     |     |
| Asn   | Lys | Asn | Thr | Glu   | Ser | Ile | Ile | Glu | Leu | Gln | Asn | Lys   | Thr | Pro | Val |
|       | 370 |     |     |       |     | 375 |     |     |     |     | 380 |       |     |     |
| Trp   | Asn | Asp | Asp | Thr   | Gln | Ser | Tyr | Val | Leu | Asn | Phe | His   | Gly | Arg | Val |
| 385   |     |     |     | 390   |     |     |     |     | 395 |     |     |       |     |     | 400 |
| Thr   | Gln | Ala | Ser | Val   | Lys | Asn | Phe | Gln | Ile | Ile | His | Gly   | Asn | Asp | Pro |
|       |     |     |     | 405   |     |     |     | 410 |     |     |     |       | 415 |     |     |
| Asp   | Tyr | Ile | Val | Met   | Gln | Phe | Gly | Arg | Val | Ala | Glu | Asp   | Val | Phe | Thr |
|       |     |     | 420 |       |     |     |     | 425 |     |     |     | 430   |     |     |     |
| Met   | Asp | Tyr | Asn | Tyr   | Pro | Leu | Cys | Ala | Leu | Gln | Ala | Phe   | Ala | Ile | Ala |
|       |     | 435 |     |       |     |     | 440 |     |     |     |     | 445   |     |     |     |
| Leu   | Ser | Ser | Phe | Asp   | Ser | Lys | Leu | Ala | Cys | Glu |     |       |     |     |     |
|       | 450 |     |     |       |     | 455 |     |     |     |     |     |       |     |     |     |

( 2 ) INFORMATION FOR SEQ ID NO:3:

( i ) SEQUENCE CHARACTERISTICS:
        ( A ) LENGTH: 2434 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:3:

```
CCTCTCCCGA  GCGCTGCACC  GCGCACAGAC  AACCGTTCTG  GGAGCCCGCG  GCCGGGGCCC      60
TGGCGTGCAG  AGAGGGCCTC  GGCGGGGCCC  AGCGGTCGGG  CCGGGGAGGA  TGCGGCCCGG     120
GGCGGCCCGA  GAGTTGAGCA  GGGTCCCCGC  GCCAGCCCCG  AGCGGTCCCG  GCCACCGGAG     180
CCGCAGCCGC  CGCCCCGCCC  CGGGAGACA   TGACTTCCAA  GCCGCATTCC  GACTGGATTC     240
CTTACAGTGT  CCTAGATGAT  GAGGGCAGCA  ACCTGAGGCA  GCAGAAGCTC  GACCGGCAGC     300
GGGCCCTGTT  GGAACAGAAG  CAGAAGAAGA  AGCGCCAAGA  GCCCTTGATG  GTACAGGCCA     360
ATGCAGATGG  ACGGCCCCGG  AGTCGGCGAG  CCCGGCAGTC  AGAGGAGCAA  GCCCCCCTGG     420
TGGAGTCCTA  CCTCAGCAGC  AGTGGCAGCA  CCAGCTACCA  AGTTCAAGAG  GCCGACTCGA     480
TTGCCAGTGT  ACAGCTGGGA  GCCACCCGCC  CACCAGCACC  AGCCTCAGCC  AAGAAATCCA     540
AGGGAGCGGC  TGCATCTGGG  GGCCAGGGTG  GAGCCCCTAG  GAAGGAGAAG  AAGGGAAAGC     600
ATAAAGGCAC  CAGCGGGCCA  GCAACTCTGG  CAGAAGACAA  GTCTGAGGCC  CAAGGCCCAG     660
TGCAGATCTT  GACTGTGGGA  CAGTCAGACC  ACGACAAGGA  TGCGGGAGAG  ACAGCAGCCG     720
GCGGGGGCGC  ACAGCCCAGT  GGGCAGGACC  TCCGTGCCAC  GATGCAGAGG  AAGGGCATCT     780
CCAGCAGCAT  GAGCTTGAC   GAGGACGAGG  ATGAGGATGA  AAACAGCTCC  AGCTCCTCCC     840
AGCTAAACAG  CAACACCCGC  CCTAGTTCTG  CCACTAGCAG  AAAGTCCATC  CGGGAGGCAG     900
CTTCAGCCCC  CAGCCCAGCC  GCCCCAGAGC  CACCAGTGGA  TATTGAGGTC  CAGGATCTAG     960
AGGAGTTTGC  ACTGAGGCCA  GCCCCACAAG  GGATCACCAT  CAAATGCCGC  ATCACTCGGG    1020
ACAAGAAGGG  GATGGACCGC  GGCATGTACC  CCACCTACTT  TCTGCACCTA  GACCGTGAGG    1080
ATGGCAAGAA  GGTGTTCCTC  CTGGCGGGCA  GGAAGAGAAA  GAAGAGTAAA  ACTTCCAATT    1140
ACCTCATCTC  TGTGGACCCA  ACAGACTTGT  CTCGGGGAGG  CGATAGCTAT  ATCGGGAAAT    1200
TGCGGTCCAA  CCTGATGGGC  ACCAAGTTCA  CCGTTTATGA  CAATGGCGTC  AACCCTCAGA    1260
AGGCATCCTC  TTCCACGCTG  GAAAGCGGAA  CCTTGCGCCA  GGAGCTGGCA  GCGGTGTGCT    1320
```

```
ATGAGACAAA TGTCCTAGGC TTCAAGGGAC CTCGGAAGAT GAGTGTGATC GTCCCAGGCA    1380
TGAACATGGT TCATGAGAGA GTCTGTATCC GCCCCCGCAA TGAACATGAG ACCCTGTTAG    1440
CACGCTGGCA GAACAAGAAC ACGGAGAGCA TCATTGAGCT GCAGAACAAG ACGCCAGTCT    1500
GGAATGATGA CACACAGTCC TATGTACTTA ACTTCCACGG CCGTGTCACA CAGGCTTCTG    1560
TGAAGAACTT CCAGATCATC CACGGCAATG ACCCGGACTA CATCGTCATG CAGTTTGGCC    1620
GGGTAGCAGA AGATGTGTTC ACCATGGATT ACAACTACCC ACTGTGTGCA CTGCAGGCCT    1680
TTGCCATTGC TCTGTCCAGC TTTGACAGCA AGCTGGCCTG CGAGTAGAGG CCCCCACTGC    1740
CTTTAGGTGG CCCAGTCCGG AGTGGAGCTT GCCTGCCTGC CAAGACAGCC CTGCCTACCC    1800
TCTGTTCATA GGCCCTCTAT GGGCTTTCTG GCCTTACCAA CCAGAGACTG GCTGCTCTGC    1860
CTCTGCTGCT GAAGCAGGGG GGACAGCAAA TGGGTATGAC AGGAGAAGAA TATTTCTGTG    1920
CCCCAAGGTC AACACACATG CCCAGTCCTG GGTCAGTCCC CTGCTGCAGT GGTGTTATCA    1980
CACCGGAAAG CCTCTTCACC TGGAGGTACA GAGGGAGAGG AAGCACAAGC CTGGCTGCTG    2040
TGGYTCAGCC ATCCACTCAG CCTACGAGTC AGAGACAGTG GGTGTCCCKG GAAGCRGGGG    2100
TACAGTGAGT GTGTGTGTAT GTACAGGGCA CTCAAGCTGT ATGTAGAAAA AGCTCTGGTG    2160
GTCAGCAGAA AGCACTCCCR CTTCAAAAGG GCCCATTAGG CCCAAAGGGG GTTAGGAGTG    2220
GTAGGGATAG GTGCGTGGCA GGTCCCTGCT AGGATTGCAG GGGCCTGGCC ATGTGTATTA    2280
GCTGGAGGCT TAGAATGCTA GCTCATTTGT TGCTACAGAT TTGCCCAGTG CTTGCAYACG    2340
TAAGAACCCA GCTCTCAAGG CCAAATATCT GAKTGGATGG GGATGATAGG AGTCATCCAG    2400
TAGACTCCCT ACATCAGGGC TCTCAGCAGC CCCA                                2434
```

( 2 ) INFORMATION FOR SEQ ID NO:4:

( i ) SEQUENCE CHARACTERISTICS:
( A ) LENGTH: 505 amino acids
( B ) TYPE: amino acid
( C ) STRANDEDNESS: double
( D ) TOPOLOGY: linear ( i i ) MOLECULE TYPE: peptide ( x i ) SEQUENCE DESCRIPTION: SEQ ID NO:4:

```
Met Thr Ser Lys Pro His Ser Asp Trp Ile Pro Tyr Ser Val Leu Asp
 1               5                  10                  15

Asp Glu Gly Ser Asn Leu Arg Gln Gln Lys Leu Asp Arg Gln Arg Ala
            20                  25                  30

Leu Leu Glu Gln Lys Gln Lys Lys Arg Gln Glu Pro Leu Met Val
        35                  40                  45

Gln Ala Asn Ala Asp Gly Arg Pro Arg Ser Arg Arg Ala Arg Gln Ser
    50                  55                  60

Glu Glu Gln Ala Pro Leu Val Glu Ser Tyr Leu Ser Ser Gly Ser
65                  70                  75                  80

Thr Ser Tyr Gln Val Gln Glu Ala Asp Ser Ile Ala Ser Val Gln Leu
            85                  90                  95

Gly Ala Thr Arg Pro Pro Ala Pro Ala Ser Ala Lys Lys Ser Lys Gly
            100                 105                 110

Ala Ala Ala Ser Gly Gly Gln Gly Ala Pro Arg Lys Glu Lys Lys
            115                 120                 125

Gly Lys His Lys Gly Thr Ser Gly Pro Ala Thr Leu Ala Glu Asp Lys
    130                 135                 140

Ser Glu Ala Gln Gly Pro Val Gln Ile Leu Thr Val Gly Gln Ser Asp
```

|   145 |       |     |     |     | 150 |     |     |     |     | 155 |     |     |     |     | 160 |
|-------|-------|-----|-----|-----|-----|-----|-----|-----|-----|-----|-----|-----|-----|-----|-----|
| His   | Asp   | Lys | Asp | Ala | Gly | Glu | Thr | Ala | Ala | Gly | Gly | Gly | Ala | Gln | Pro |
|       |       |     |     | 165 |     |     |     | 170 |     |     |     |     | 175 |     |     |

Ser Gly Gln Asp Leu Arg Ala Thr Met Gln Arg Lys Gly Ile Ser Ser
            180                 185                 190

Ser Met Ser Phe Asp Glu Asp Glu Asp Glu Asn Ser Ser Ser
        195             200             205

Ser Ser Gln Leu Asn Ser Asn Thr Arg Pro Ser Ser Ala Thr Ser Arg
    210             215                 220

Lys Ser Ile Arg Glu Ala Ala Ser Ala Pro Ser Pro Ala Ala Pro Glu
225             230             235                 240

Pro Pro Val Asp Ile Glu Val Gln Asp Leu Glu Glu Phe Ala Leu Arg
            245             250             255

Pro Ala Pro Gln Gly Ile Thr Ile Lys Cys Arg Ile Thr Arg Asp Lys
        260             265                 270

Lys Gly Met Asp Arg Gly Met Tyr Pro Thr Tyr Phe Leu His Leu Asp
    275                 280             285

Arg Glu Asp Gly Lys Lys Val Phe Leu Leu Ala Gly Arg Lys Arg Lys
    290             295             300

Lys Ser Lys Thr Ser Asn Tyr Leu Ile Ser Val Asp Pro Thr Asp Leu
305             310             315                 320

Ser Arg Gly Gly Asp Ser Tyr Ile Gly Lys Leu Arg Ser Asn Leu Met
            325             330             335

Gly Thr Lys Phe Thr Val Tyr Asp Asn Gly Val Asn Pro Gln Lys Ala
        340             345             350

Ser Ser Ser Thr Leu Glu Ser Gly Thr Leu Arg Gln Glu Leu Ala Ala
    355             360             365

Val Cys Tyr Glu Thr Asn Val Leu Gly Phe Lys Gly Pro Arg Lys Met
370             375             380

Ser Val Ile Val Pro Gly Met Asn Met Val His Glu Arg Val Cys Ile
385             390             395             400

Arg Pro Arg Asn Glu His Glu Thr Leu Leu Ala Arg Trp Gln Asn Lys
            405             410             415

Asn Thr Glu Ser Ile Ile Glu Leu Gln Asn Lys Thr Pro Val Trp Asn
        420             425             430

Asp Asp Thr Gln Ser Tyr Val Leu Asn Phe His Gly Arg Val Thr Gln
        435             440             445

Ala Ser Val Lys Asn Phe Gln Ile Ile His Gly Asn Asp Pro Asp Tyr
    450             455             460

Ile Val Met Gln Phe Gly Arg Val Ala Glu Asp Val Phe Thr Met Asp
465             470             475             480

Tyr Asn Tyr Pro Leu Cys Ala Leu Gln Ala Phe Ala Ile Ala Leu Ser
            485             490             495

Ser Phe Asp Ser Lys Leu Ala Cys Glu
            500             505

( 2 ) INFORMATION FOR SEQ ID NO:5:

( i ) SEQUENCE CHARACTERISTICS:
        ( A ) LENGTH: 480 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:5:

```
ACTTCCAGAT  CATCCACGGC  AATGACCTTG  AGTGTTGCCA  CTCCCTGTTT  TTGATGTTGT      60
ACGCATGGTG  CCCAGCCCCC  ACCCCACCCC  CAATCCCCTG  ATCTGGTCCA  TATCAGCCAG     120
TGATGGGATG  TGGGTATATG  GCTTTTGTTA  GAACTTTCTA  ACTGTAGTGA  TCTAGAGTCC     180
TGCCCCTAGT  GCCCTGCATG  TCTGGGGCTT  GGGAATACCC  TTTAAATGGA  TGTCTTTTCT     240
CTCCTGGGCC  CTGCTGTCTG  TGTGCATCTC  CCCCCTTCAC  CCTCTTGCTT  CATAATGTTT     300
CTCTTGAACC  TTTGTTTTGT  TCATCCTTTC  GATCTCTTTG  GCATTTCTGC  TTTCTCCTTC     360
CCTCTTGTGG  CCCATGTCTT  ACCTGGTCTC  CCTGTCTCCA  CCAATTCTTG  CTTGGTGCAT     420
GCCACAGCGG  ACTACATCGT  CATGCAGTTT  GGCCGGGTAG  CAGAAGATGT  GTTCACCATG     480
```

( 2 ) INFORMATION FOR SEQ ID NO:6:

( i ) SEQUENCE CHARACTERISTICS:
        ( A ) LENGTH: 1426 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:6:

```
CAGAAGAAGA  AGCGCCAGGA  GCCCCTGATG  GTGCAGGCCA  ATGCAGATGG  GCGGCCCCGG      60
AGCCGGCGGG  CCCGGCAGTC  AGAGGAACAA  GCCCCCCTGG  TGGAGTCCTA  CCTCAGCAGC     120
AGTGGCAGCA  CCAGCTACCA  AGTTCAAGAG  GCCGACTCAC  TCGCCAGTGT  GCAGCTGGGA     180
GCCACGCGCC  CAACAGCACC  AGCTTCAGCC  AAGAGAACCA  AGGCGGCAGC  TACAGCAGGG     240
GGCCAGGGCG  GCGCCGCTAG  GAAGGAGAAG  AAGGGAAAGC  ACAAAGGCAC  CAGCGGGCCA     300
GCAGCACTGG  CAGAAGACAA  GTCTGAGGCC  CAAGGCCCAG  TGCAGATTCT  GACTGTGGGC     360
CAGTCAGACC  ACGCCCAGGA  CGCAGGGGAG  ACGGCAGCTG  GTGGGGGCGA  ACGGCCCAGC     420
GGGCAGGATC  TCCGTGCCAC  GATGCAGAGG  AAGGGCATCT  CCAGCAGCAT  GAGCTTTGAC     480
GAGGATGAGG  AGGATGAGGA  GGAGAATAGC  TCCAGCTCCT  CCCAGCTAAA  TAGTAACACC     540
CGCCCCAGCT  CTGCTACTAG  CAGGAAGTCC  GTCAGGGAGG  CAGCCTCAGC  CCCTAGCCCA     600
ACAGCTCCAG  AGCAACCAGT  GGACGTTGAG  GTCCAGGATC  TTGAGGAGTT  TGCACTGAGG     660
CCGGCCCCCC  AGGGTATCAC  CATCAAATGC  CGCATCACTC  GGGACAAGAA  AGGGATGGAC     720
CGGGGCATGT  ACCCCACCTA  CTTTCTGCAC  CTGGACCGTG  AGGATGGGAA  GAAGGTGTTC     780
CTCCTGGCGG  GAAGGAAGAG  AAAGAAGAGT  AAAACTTCCA  ATTACCTCAT  CTCTGTGGAC     840
CCAACAGACT  TGTCTCGAGG  AGGGGACAGC  TATATCGGGA  AACTGCGGTC  CAACTTGATG     900
GGCACCAAGT  TCACTGTTTA  TGACAATGGA  GTCAACCCTC  AGAAGGCCTC  ATCCTCCACT     960
TTGGAAAGTG  GAACCTTACG  TCAGGAGCTG  GCAGCTGTGT  GCTACGAGAC  AAACGTCTTA    1020
GGCTTCAAGG  GGCCTCGGAA  GATGAGCGTG  ATTGTCCCAG  GCATGAACAT  GGTCCATGAG    1080
AGAGTCTCTA  TCCGCCCCCG  CAACGAGCAT  GAGACACTGC  TAGCACGCTG  GCAGAATAAG    1140
AACACGGAGA  GTATCATCGA  GCTGCAAAAC  AAGACACCTG  TCTGGAATGA  TGACACACAG    1200
TCCTATGTAC  TCAACTTCCA  TGGGCGCGTC  ACACAGGCCT  CCGTGAAGAA  CTTCCAGATC    1260
ATCCATGGCA  ATGACCCGGA  CTACATCGTG  ATGCAGTTTG  GCCGGGTAGC  AGAGGATGTG    1320
TTCACCATGG  ATTACAACTA  CCCGCTGTGT  GCACTGCAGG  CCTTTGCCAT  TGCCCTGTCC    1380
AGCTTCGACA  GCAAGCTGGC  GTGCGAGTAG  AGGCCTCTTC  GTGCCC                   1426
```

( 2 ) INFORMATION FOR SEQ ID NO:7:

( i ) SEQUENCE CHARACTERISTICS:
 ( A ) LENGTH: 460 amino acids
 ( B ) TYPE: amino acid
 ( C ) STRANDEDNESS: double
 ( D ) TOPOLOGY: linear ( i i ) MOLECULE TYPE: peptide ( x i ) SEQUENCE DESCRIPTION: SEQ ID NO:7:

```
Met Val Gln Ala Asn Ala Asp Gly Arg Pro Arg Ser Arg Arg Ala Arg
 1               5                  10                  15
Gln Ser Glu Glu Gln Ala Pro Leu Val Glu Ser Tyr Leu Ser Ser Ser
             20                  25                  30
Gly Ser Thr Ser Tyr Gln Val Gln Glu Ala Asp Ser Leu Ala Ser Val
         35                  40                  45
Gln Leu Gly Ala Thr Arg Pro Thr Ala Pro Ala Ser Ala Lys Arg Thr
     50                  55                  60
Lys Ala Ala Ala Thr Ala Gly Gln Gly Gly Ala Ala Arg Lys Glu
 65                  70                  75                  80
Lys Lys Gly Lys His Lys Gly Thr Ser Gly Pro Ala Ala Leu Ala Glu
                     85                  90                  95
Asp Lys Ser Glu Ala Gln Gly Pro Val Gln Ile Leu Thr Val Gly Gln
             100                 105                 110
Ser Asp His Ala Gln Asp Ala Gly Glu Thr Ala Ala Gly Gly Gly Glu
         115                 120                 125
Arg Pro Ser Gly Gln Asp Leu Arg Ala Thr Met Gln Arg Lys Gly Ile
     130                 135                 140
Ser Ser Ser Met Ser Phe Asp Glu Asp Glu Asp Glu Glu Glu Asn
 145                 150                 155                 160
Ser Ser Ser Ser Ser Gln Leu Asn Ser Asn Thr Arg Pro Ser Ser Ala
                     165                 170                 175
Thr Ser Arg Lys Ser Val Arg Glu Ala Ala Ser Ala Pro Ser Pro Thr
             180                 185                 190
Ala Pro Glu Gln Pro Val Asp Val Glu Val Gln Asp Leu Glu Glu Phe
         195                 200                 205
Ala Leu Arg Pro Ala Pro Gln Gly Ile Thr Ile Lys Cys Arg Ile Thr
     210                 215                 220
Arg Asp Lys Lys Gly Met Asp Arg Gly Met Tyr Pro Thr Tyr Phe Leu
 225                 230                 235                 240
His Leu Asp Arg Glu Asp Gly Lys Lys Val Phe Leu Leu Ala Gly Arg
                     245                 250                 255
Lys Arg Lys Lys Ser Lys Thr Ser Asn Tyr Leu Ile Ser Val Asp Pro
             260                 265                 270
Thr Asp Leu Ser Arg Gly Gly Asp Ser Tyr Ile Gly Lys Leu Arg Ser
         275                 280                 285
Asn Leu Met Gly Thr Lys Phe Thr Val Tyr Asp Asn Gly Val Asn Pro
     290                 295                 300
Gln Lys Ala Ser Ser Ser Thr Leu Glu Ser Gly Thr Leu Arg Gln Glu
 305                 310                 315                 320
Leu Ala Ala Val Cys Tyr Glu Thr Asn Val Leu Gly Phe Lys Gly Pro
                     325                 330                 335
Arg Lys Met Ser Val Ile Val Pro Gly Met Asn Met Val His Glu Arg
             340                 345                 350
Val Ser Ile Arg Pro Arg Asn Glu His Glu Thr Leu Leu Ala Arg Trp
         355                 360                 365
```

| | | | | | | | | | | | | | | |
|---|---|---|---|---|---|---|---|---|---|---|---|---|---|---|
| Gln | Asn<br>370 | Lys | Asn | Thr | Glu | Ser<br>375 | Ile | Ile | Glu | Leu | Gln<br>380 | Asn | Lys | Thr | Pro |
| Val<br>385 | Trp | Asn | Asp | Asp | Thr<br>390 | Gln | Ser | Tyr | Val | Leu<br>395 | Asn | Phe | His | Gly | Arg<br>400 |
| Val | Thr | Gln | Ala | Ser<br>405 | Val | Lys | Asn | Phe | Gln<br>410 | Ile | Ile | His | Gly | Asn<br>415 | Asp |
| Pro | Asp | Tyr | Ile<br>420 | Val | Met | Gln | Phe | Gly<br>425 | Arg | Val | Ala | Glu | Asp<br>430 | Val | Phe |
| Thr | Met | Asp<br>435 | Tyr | Asn | Tyr | Pro | Leu<br>440 | Cys | Ala | Leu | Gln | Ala<br>445 | Phe | Ala | Ile |
| Ala | Leu | Ser<br>450 | Ser | Phe | Asp | Ser<br>455 | Lys | Leu | Ala | Cys | Glu<br>460 | | | | |

( 2 ) INFORMATION FOR SEQ ID NO:8:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer"

( x i ) SEQUENCE DESCRIPTION: SEQ ID NO:8:

TTCACAAAAG CACACCTGG        19

( 2 ) INFORMATION FOR SEQ ID NO:9:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer"

( x i ) SEQUENCE DESCRIPTION: SEQ ID NO:9:

GTCCCAAGGA TGGAGACCT        19

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer"

( x i ) SEQUENCE DESCRIPTION: SEQ ID NO:10:

TGGTGAGCAA AACAAGGAAC        20

( 2 ) INFORMATION FOR SEQ ID NO:11:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer"

( x i ) SEQUENCE DESCRIPTION: SEQ ID NO:11:

TGGGGAAAGC AATTTCTGG 19

(2) INFORMATION FOR SEQ ID NO:12:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:12:

GCCTGTCAGC AAGGACCTT 19

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:13:

CCATGTCCCA AACAAGATGG 20

(2) INFORMATION FOR SEQ ID NO:14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:14:

ACCTGAGGCA GCAGAAGCT 19

(2) INFORMATION FOR SEQ ID NO:15:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:15:

CAGCCAGTCT CTGGTTGGT 19

(2) INFORMATION FOR SEQ ID NO:16:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:16:

TGCAGAACAA GACGCCAGT                                                              19

( 2 ) INFORMATION FOR SEQ ID NO:17:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer"

( x i ) SEQUENCE DESCRIPTION: SEQ ID NO:17:

GATGTTGTAC GCATGGTGC                                                              19

( 2 ) INFORMATION FOR SEQ ID NO:18:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer"

( x i ) SEQUENCE DESCRIPTION: SEQ ID NO:18:

TGGAGACAGG GAGACCAGG                                                              19

( 2 ) INFORMATION FOR SEQ ID NO:19:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer"

( x i ) SEQUENCE DESCRIPTION: SEQ ID NO:19:

GATGGCAAGA AGGTGTTCC                                                              19

( 2 ) INFORMATION FOR SEQ ID NO:20:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer"

( x i ) SEQUENCE DESCRIPTION: SEQ ID NO:20:

TCATTGCGGG GGCGGATAC                                                              19

( 2 ) INFORMATION FOR SEQ ID NO:21:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer"

( x i ) SEQUENCE DESCRIPTION: SEQ ID NO:21:

```
ATGGTGAAGG TCGGTGTGAA                                                                                        20
```

( 2 ) INFORMATION FOR SEQ ID NO:22:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer"

( x i ) SEQUENCE DESCRIPTION: SEQ ID NO:22:

```
ACCAGTAGAC TCCACGACAT                                                                                        20
```

( 2 ) INFORMATION FOR SEQ ID NO:23:

( i ) SEQUENCE CHARACTERISTICS:
        ( A ) LENGTH: 171 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:23:

```
GGTCATTGCC GTGGATGATC TGGAAGTTCT TCACAGAAGC CTGTGTGACA CGGCCGTGGA        60
AGTTAAGTAC ATAGGACTGT GTGTCATCAT TCCAGACGGC GTCTTGTTCT GCAGCTCAAT       120
GATGCTCTCC GTGTTCTTGT TCTGCCAGCG TGCTAACAGG GTCTCATGTT C                171
```

( 2 ) INFORMATION FOR SEQ ID NO:24:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

```
GAGACAAATG TCCTAGGCTT CAAGGGACCT CGGAAGATGA GTGTGATCGT CCCAGGCATG        60
AACATGGTTC ATGAGAGAGT CTGTATCCGC CCCCGCAAT                               99
```

( 2 ) INFORMATION FOR SEQ ID NO:25:

( i ) SEQUENCE CHARACTERISTICS:
        ( A ) LENGTH: 33 amino acids
        ( B ) TYPE: amino acid
        ( C ) STRANDEDNESS: double
        ( D ) TOPOLOGY: linear ( i i ) MOLECULE TYPE: peptide ( x i ) SEQUENCE DESCRIPTION: SEQ ID NO:25:

```
Asn Phe Gln Ile Ile His Gly Asn Asp Leu Glu Cys Cys His Ser Leu
 1               5                  10                  15
Phe Leu Met Leu Tyr Ala Trp Cys Pro Ala Pro Thr Pro Pro Ile
                20                  25                  30
Pro
```

( 2 ) INFORMATION FOR SEQ ID NO:26:

( i ) SEQUENCE CHARACTERISTICS:
        ( A ) LENGTH: 3060 base pairs ( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:26:

```
CATCCCTTAA ACCCACTCCA TCCTGTGGCC ACGATGGGGG CCAGGACACC TTTGCCTTCT        60
TTCTGGGTTT CTTTCTTTGC CGAGACAGGG ATTTGTTCC  CAGGAGGCAC TCCCTGGCCC       120
ATGGGATCTC AGCATTCAAA GCAGCACAGG AAACCTGGGC CCCTGAAACG GGGCCACCGA       180
AGAGATCGGA GAACAACCAG GAGGAAGTAC TGGAAGGAAG GAAGGGAGAT CGCTCGTGTC       240
TTAGATGATG AGGGCAGAAA CCTGAGGCAG CAGAAGCTTG ATCGGCAGCG GGCCCTGCTG       300
GAGCAGAAGC AGAAGAAGAA GCGCCAGGAG CCCCTGATGG TGCAGGCCAA TGCAGATGGG       360
CGGCCCCGGA GCCGGCGGGC CCGGCAGTCA GAGGAACAAG CCCCCCTGGT GGAGTCCTAC       420
CTCAGCAGCA GTGGCAGCAC CAGCTACCAA GTTCAAGAGG CCGACTCACT CGCCAGTGTG       480
CAGCTGGGAG CCACGCGCCC AACAGCACCA GCTTCAGCCA AGAGAACCAA GGCGGCAGCT       540
ACAGCAGGGG GCCAGGGCGG CGCCGCTAGG AAGGAGAAGA AGGGAAAGCA CAAAGGCACC       600
AGCGGGCCAG CAGCACTGGC AGAAGACAAG TCTGAGGCCC AAGGCCCAGT GCAGATTCTG       660
ACTGTGGGCC AGTCAGACCA CGCCCAGGAC GCAGGGGAGA CGGCAGCTGG TGGGGGCGAA       720
CGGCCCAGCG GGCAGGATCT CCGTGCCACG ATGCAGAGGA AGGGCATCTC CAGCAGCATG       780
AGCTTTGACG AGGATGAGGA GGATGAGGAG GAGAATAGCT CCAGCTCCTC CCAGCTAAAT       840
AGTAACACCC GCCCCAGCTC TGCTACTAGC AGGAAGTCCG TCAGGGAGGC AGCCTCAGCC       900
CCTAGCCCAA CAGCTCCAGA GCAACCAGTG GACGTTGAGG TCCAGGATCT TGAGGAGTTT       960
GCACTGAGGC CGGCCCCCA  GGGTATCACC ATCAAATGCC GCATCACTCG GGACAAGAAA      1020
GGGATGGACC GGGGCATGTA CCCCACCTAC TTTCTGCACC TGGACCGTGA GGATGGGAAG      1080
AAGGTGTTCC TCCTGGCGGG AAGGAAGAGA AAGAAGAGTA AAACTTCCAA TTACCTCATC      1140
TCTGTGGACC CAACAGACTT GTCTCGAGGA GGGGACAGCT ATATCGGGAA ACTGCGGTCC      1200
AACTTGATGG GCACCAAGTT CACTGTTTAT GACAATGGAG TCAACCCTCA GAAGGCCTCA      1260
TCCTCCACTT TGGAAAGTGG AACCTTACGT CAGGAGCTGG CAGCTGTGTG CTACGAGACA      1320
AACGTCTTAG GCTTCAAGGG GCCTCGGAAG ATGAGCGTGA TTGTCCCAGG CATGAACATG      1380
GTCCATGAGA GAGTCTCTAT CCGCCCCCGC AACGAGCATG AGACACTGCT AGCACGCTGG      1440
CAGAATAAGA ACACGGAGAG TATCATCGAG CTGCAAAACA AGACACCTGT CTGGAATGAT      1500
GACACACAGT CCTATGTACT CAACTTCCAT GGGCGCGTCA CACAGGCCTC CGTGAAGAAC      1560
TTCCAGATCA TCCATGGCAA TGACCCGGAC TACATCGTGA TGCAGTTTGG CCGGGTAGCA      1620
GAGGATGTGT TCACCATGGA TTACAACTAC CCGCTGTGTG CACTGCAGGC CTTTGCCATT      1680
GCCCTGTCCA GCTTCGACAG CAAGCTGGCG TGCGAGTAGA GGCCTCTTCG TGCCCTTTGG      1740
GGTTGCCCAG CCTGGAGCGG AGCTTGCCTG CCTGCCTGTG GAGACAGCCC TGCCTATCCT      1800
CTGTATATAG GCCTTCCGCC AGATGAAGCT TTGGCCCTCA GTGGGCTCCC CTGGCCCAGC      1860
CAGCCAGGAA CTGGCTCCTT TGCCTCTGCT ACTGAGCAGG GGAGTAGTGG AGAGCGGGTG      1920
GGTGGGTGTG AAGGGATGAG AATAATTCTT TCCATGCCAC GAGATCAACA CACACTCCCA      1980
CCCTTGGGGT AGTAGTGTGT TGTAGTCGTA CTTACCAAGC TGAGCAACCT CTTCAGCTGG      2040
GAAGGCCGCA AGAGGCATAG AGGGAGAGGA AGCACACTGC AGGGCTGCTG TGGCCCAGTC      2100
GTCCGCTCAG CCAAGGAGTC AGATGGCAAT GGGTACTCCA GCAGGTAGGG GCACAGTGAA      2160
```

-continued

| | | | | | |
|---|---|---|---|---|---|
| TGTGTGTATG | TATGAAGGCC | ACATCAACTT | TATGTAGCAA | AGGGCTTGGT | GGCCAAGCCT | 2220 |
| GGCCCTTAAA | CAACTGCAGA | AAGCCCTTCA | ACTTCAGAAG | GCCTCACTCA | AGCCTGAGAG | 2280 |
| AAGTTGGGAG | GGTGGTGGGG | ACAGGTAAGT | GGCAGGACCC | TGTCAGGATT | GCAGGTGCCT | 2340 |
| GGCTTGCTGT | GGCTATGGGA | ATCAGCTGGT | GGCTAGGTTT | CTAGCGCATT | TGATTTCTCC | 2400 |
| AGGTTTGCTG | TGTCTCACAG | AGGCAGTAGG | AACCCAGCTC | TCAGGGCTGT | CTTGGTGGAT | 2460 |
| GGGCCCTGCA | AGACACAGGC | TCAGCATGCA | GAAGTGCATG | AACAGGGTCC | CTGGATCAGG | 2520 |
| GTTGTTCTGG | GAGTCCTGTC | AGCTTCCCCA | GGAGCTCTCT | GCTGAGCAGC | CCAGCACAAC | 2580 |
| CCCCAGGAAA | CACAAATGGG | GTCCAGGTCA | CCAGCCTGAC | TGCACACAGC | TAGGCATGCC | 2640 |
| TGGGAATCCT | GCTGCCAGAG | AACCATTCCC | AAGCCATGGC | ATGCTCCTTG | AAGAATCTCT | 2700 |
| CCTCTCTCTC | TCTCTCTGGA | AAGACCCAAC | TTCCTCACTG | CTGTCAGCCA | AGTCATGGTT | 2760 |
| GGTAACCATG | TAGGTTCTTG | GGAGGGAATG | GGACAGGGTG | AATAAAGCAG | GGAATATTTC | 2820 |
| CGGAATTCCA | CAAGAGATCA | GCAGTGGCAG | GACCCTTAGG | AATCTAGTAC | AACCTTGTTG | 2880 |
| CTTTAGGTGA | GTCACACTCA | GAAAATGGGG | CTTGCCCTGG | GTCACCTAGC | TGGTTAATGG | 2940 |
| CAGCATTCAG | TAACTTCAAG | TTCTCTTGAT | TTCTTTGTTC | CCACTGTCCC | CCAAGAAACT | 3000 |
| AGTATCTCTG | GCCTCCTGGG | GCCCATTCTG | CATGCCCTCC | CCACTTCCCC | CCCGGAATTC | 3060 |

( 2 ) INFORMATION FOR SEQ ID NO:27:

( i ) SEQUENCE CHARACTERISTICS:
        ( A ) LENGTH: 561 amino acids
        ( B ) TYPE: amino acid
        ( C ) STRANDEDNESS: double
        ( D ) TOPOLOGY: linear ( i i ) MOLECULE TYPE: peptide ( x i ) SEQUENCE DESCRIPTION: SEQ ID NO:27:

```
Met Gly Ala Arg Thr Pro Leu Pro Ser Phe Trp Val Ser Phe Phe Ala
 1               5                  10                  15

Glu Thr Gly Ile Leu Phe Pro Gly Gly Thr Pro Trp Pro Met Gly Ser
            20                  25                  30

Gln His Ser Lys Gln His Arg Lys Pro Gly Pro Leu Lys Arg Gly His
        35                  40                  45

Arg Arg Asp Arg Arg Thr Thr Arg Arg Lys Tyr Trp Lys Glu Gly Arg
    50                  55                  60

Glu Ile Ala Arg Val Leu Asp Asp Glu Gly Arg Asn Leu Arg Gln Gln
65                  70                  75                  80

Lys Leu Asp Arg Gln Arg Ala Leu Leu Glu Gln Lys Gln Lys Lys Lys
                85                  90                  95

Arg Gln Glu Pro Leu Met Val Gln Ala Asn Ala Asp Gly Arg Pro Arg
            100                 105                 110

Ser Arg Arg Ala Arg Gln Ser Glu Glu Gln Ala Pro Leu Val Glu Ser
        115                 120                 125

Tyr Leu Ser Ser Ser Gly Ser Thr Ser Tyr Gln Val Gln Glu Ala Asp
    130                 135                 140

Ser Leu Ala Ser Val Gln Leu Gly Ala Thr Arg Pro Thr Ala Pro Ala
145                 150                 155                 160

Ser Ala Lys Arg Thr Lys Ala Ala Ala Thr Ala Gly Gly Gln Gly Gly
                165                 170                 175

Ala Ala Arg Lys Glu Lys Lys Gly Lys His Lys Gly Thr Ser Gly Pro
            180                 185                 190

Ala Ala Leu Ala Glu Asp Lys Ser Glu Ala Gln Gly Pro Val Gln Ile
```

|     |     |     |     |     | 195 |     |     |     | 200 |     |     |     |     | 205 |
| --- | --- | --- | --- | --- | --- | --- | --- | --- | --- | --- | --- | --- | --- | --- |
| Leu | Thr | Val | Gly | Gln | Ser | Asp | His | Ala | Gln | Asp | Ala | Gly | Glu | Thr | Ala |
| 210 | | | | | 215 | | | | 220 | | | | | | |
| Ala | Gly | Gly | Gly | Glu | Arg | Pro | Ser | Gly | Gln | Asp | Leu | Arg | Ala | Thr | Met |
| 225 | | | | | 230 | | | | 235 | | | | | | 240 |
| Gln | Arg | Lys | Gly | Ile | Ser | Ser | Ser | Met | Ser | Phe | Asp | Glu | Asp | Glu | Glu |
| | | | | 245 | | | | | 250 | | | | | 255 | |
| Asp | Glu | Glu | Glu | Asn | Ser | Ser | Ser | Ser | Gln | Leu | Asn | Ser | Asn | Thr |
| | | | 260 | | | | | 265 | | | | 270 | | |
| Arg | Pro | Ser | Ser | Ala | Thr | Ser | Arg | Lys | Ser | Val | Arg | Glu | Ala | Ala | Ser |
| | 275 | | | | | 280 | | | | | 285 | | | | |
| Ala | Pro | Ser | Pro | Thr | Ala | Pro | Glu | Gln | Pro | Val | Asp | Val | Glu | Val | Gln |
| 290 | | | | | 295 | | | | 300 | | | | | | |
| Asp | Leu | Glu | Glu | Phe | Ala | Leu | Arg | Pro | Ala | Pro | Gln | Gly | Ile | Thr | Ile |
| 305 | | | | | 310 | | | | 315 | | | | | | 320 |
| Lys | Cys | Arg | Ile | Thr | Arg | Asp | Lys | Lys | Gly | Met | Asp | Arg | Gly | Met | Tyr |
| | | | | 325 | | | | | 330 | | | | | 335 | |
| Pro | Thr | Tyr | Phe | Leu | His | Leu | Asp | Arg | Glu | Asp | Gly | Lys | Lys | Val | Phe |
| | | | 340 | | | | | 345 | | | | | 350 | | |
| Leu | Leu | Ala | Gly | Arg | Lys | Arg | Lys | Lys | Ser | Lys | Thr | Ser | Asn | Tyr | Leu |
| | | | 355 | | | | 360 | | | | | 365 | | | |
| Ile | Ser | Val | Asp | Pro | Thr | Asp | Leu | Ser | Arg | Gly | Gly | Asp | Ser | Tyr | Ile |
| | 370 | | | | | 375 | | | | | 380 | | | | |
| Gly | Lys | Leu | Arg | Ser | Asn | Leu | Met | Gly | Thr | Lys | Phe | Thr | Val | Tyr | Asp |
| 385 | | | | | 390 | | | | 395 | | | | | | 400 |
| Asn | Gly | Val | Asn | Pro | Gln | Lys | Ala | Ser | Ser | Ser | Thr | Leu | Glu | Ser | Gly |
| | | | | 405 | | | | | 410 | | | | | 415 | |
| Thr | Leu | Arg | Gln | Glu | Leu | Ala | Ala | Val | Cys | Tyr | Glu | Thr | Asn | Val | Leu |
| | | | 420 | | | | | 425 | | | | | 430 | | |
| Gly | Phe | Lys | Gly | Pro | Arg | Lys | Met | Ser | Val | Ile | Val | Pro | Gly | Met | Asn |
| | | 435 | | | | 440 | | | | | 445 | | | | |
| Met | Val | His | Glu | Arg | Val | Ser | Ile | Arg | Pro | Arg | Asn | Glu | His | Glu | Thr |
| 450 | | | | | 455 | | | | 460 | | | | | | |
| Leu | Leu | Ala | Arg | Trp | Gln | Asn | Lys | Asn | Thr | Glu | Ser | Ile | Ile | Glu | Leu |
| 465 | | | | | 470 | | | | 475 | | | | | | 480 |
| Gln | Asn | Lys | Thr | Pro | Val | Trp | Asn | Asp | Asp | Thr | Gln | Ser | Tyr | Val | Leu |
| | | | | 485 | | | | 490 | | | | | 495 | | |
| Asn | Phe | His | Gly | Arg | Val | Thr | Gln | Ala | Ser | Val | Lys | Asn | Phe | Gln | Ile |
| | | | 500 | | | | | 505 | | | | | 510 | | |
| Ile | His | Gly | Asn | Asp | Pro | Asp | Tyr | Ile | Val | Met | Gln | Phe | Gly | Arg | Val |
| | | 515 | | | | | 520 | | | | | 525 | | | |
| Ala | Glu | Asp | Val | Phe | Thr | Met | Asp | Tyr | Asn | Tyr | Pro | Leu | Cys | Ala | Leu |
| | 530 | | | | | 535 | | | | | 540 | | | | |
| Gln | Ala | Phe | Ala | Ile | Ala | Leu | Ser | Ser | Phe | Asp | Ser | Lys | Leu | Ala | Cys |
| 545 | | | | | 550 | | | | 555 | | | | | | 560 |
| Glu | | | | | | | | | | | | | | | |

( 2 ) INFORMATION FOR SEQ ID NO:28:

( i ) SEQUENCE CHARACTERISTICS:
        ( A ) LENGTH: 1551 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:28:

```
CTTGAGGATT CAGTCTGGTC CTGAAGGGTT TGGGGGGAGA CTGCGACCAG AAGATGTTTC      60
CATGTCCTAA TTAATGGGTG ATGGTGGTTG TTAGTCTGAC TGTTGCCACG GTGATGAAGG     120
GAGACATCCA AGTGCTGGTT TCAGTACTGA GGCGAATACA GGGAATTTCA ACAGGCTCCA     180
GGTCTTACTA TGCAGCCTGA AGTGGGACCA TCCCTTAAAC CCACTCCATC CTGTGGCCAC     240
GATGGGGGCC AGGACACCTT TGCCTTCTTT CTGGGTTTCT TTCTTTGCCG AGACAGGGAT     300
TTTGTTCCCA GGAGGCACTC CCTGGCCCAT GGGATCTCAG CATTCAAAGC AGCACAGGAA     360
ACCTGGGCCC CTGAAACGGG GCCACCGAAG AGATCGGTAA GCTTTCAACA TCCTGCCTTT     420
AGCCCATGGG CCCAACCATT GCGTCAGCTC CACCCACCCA CCCTCACTGA CCTCAACCCT     480
TTACAGTCCC AAGGCCTCCC CTTCCTGATG GTGCTGCTCC CCTATCACCA CGTGGAGCCC     540
CACAGGTATA TCCCCGCAAA CCCCTCTTGC TCCAGACAGG TGATCAGGGA GGCTTCATTA     600
CTCCAGGAGC TGCCCAGGAC CTCAGGGAGG TCCCCACCA TGGGAGTAAG GGCCTCTCCC     660
CCAGCCTCCA GGGCTCCGGC AGCTCCACAC TCCGGCCCTC TGCCTCTTCT GGAGGGCTCC     720
TCCTTCCAGC TTCTGCCTGT CTCCCCACCC CCAGTGCTT CATTCCATG GCTCAGGTCA     780
TCACTGCCCT CATCTGGACT GCCTGCCTGC CTGCCTGCCA TCCGGGCCC ACAGAGTGAG     840
CACTCTATGG AAGTCCCTCT ACCCTGATCC ATCACGTAAC TCACCTACTG AGGCAGCTGA     900
GACCAGGGCA CTGAAGGAGG CCTTGAGTGA CCAGGTGTGG CCAGGCAGCA GGCAGGGATG     960
ATGAGGTGAG GCTGCAAGGA TGTGGAGAGT CACCCCTTCT TTTCCTCCTC AGGAGAACAA    1020
CCAGGAGGAA GTACTGGAAG GAAGGAAGGG AGATCGCTCG TGTCTTAGAT GATGAGGGCA    1080
GAAACCTGAG GCAGCAGAAG CTTGATCGGC AGCGGGCCCT GCTGGAGCAG AAGCAGAAGA    1140
AGAAGCGCCA GGAGCCCCTG ATGGTGCAGG CCAATGCAGA TGGGCGGCCC CGGAGCCGGC    1200
GGGCCCGGCA GTCAGAGGAA CAAGCCCCCC TGGTGGAGTC CTACCTCAGC AGCAGTGGCA    1260
GCACCAGCTA CCAAGTTCAA GAGGCCGACT CACTCGCCAG TGTGCAGCTG GGAGCCACGC    1320
GCCCAACAGC ACCAGCTTCA GCCAAGAGAA CCAAGGCGGC AGCTACAGCA GGGGCCAGG    1380
GCGGCGCCGC TAGGAAGGAG AAGAAGGGAA AGCACAAAGG TCAGCTCACA TTCTCTACAG    1440
CCCTGCCCAG CAGGCTGGCC TCCACTGTAG GGCTGGGGAA GGTTTGTCCC CTGACTTGGA    1500
GGGGACGGAT AGGATCACCC TCTCTTGACT CACCTTATCT CCTCTTCTTT G            1551
```

OBESITY ASSOCIATED GENES This application is a C.I.P. of application Ser. No. 630/592, filed Apr. 10, 1996.

TECHNICAL FIELD

The field of this invention is genes associated with obesity in mammals.

BACKGROUND

Human obesity is a widespread and serious disorder, affecting a high percentage of the adult population in developed countries. In spite of an association with heart disease, type II diabetes, cancer, and other conditions, few persons are able to permanently achieve significant weight loss. Failure to treat obesity may be at least partially attributed to the complexity of the disease. Genetic, psychological and environmental factors all play a role in individual patterns of weight gain or loss, making it exceedingly difficult to define the contribution of any single element.

An understanding of the genetic factors that underlie obesity may aid in treatment. However, defining the exact genetic loci involved in a human polygenic trait requires extensive family studies. Because there are so many genes that can affect the single trait of obesity, in humans it may be virtually impossible to statistically determine the contribution of one locus. An attempt at such mapping studies can be further complicated by the interaction and linkage of genes. Also, environmental effects cannot be assumed to be the same for all genotypes. As an alternative to the complexities of human genetic mapping, animal models may be useful.

Inbred mouse strains are widely used in genetic and immunological studies. Inbred animals are isogenic at all autosomal loci, that is, not only are individuals of the strain genetically identical to each other, but both copies of each diploid gene are also identical. By crossing different inbred strains, it is possible to generate a detailed genetic map of a region. The genetic map can then be used as a basis for physical characterization of the region. However, even the smallest of measurable genetic intervals generally contains somewhere between 5 and 100 different open reading frames. A gene will consist of one or a combination of open reading frames. Each candidate gene must be carefully evaluated for differences between the normal and mutant genotype. Once the mouse gene responsible for the mutant phenotype is identified, it can then be used to identify the human counterpart, and for analysis of the structure and function of the gene product.

Mouse models for obesity include obese (ob), agouti (wt), tubby (tub), fat and diabetes (db). These animal models are extremely useful for their ability to simplify the heritability of an otherwise very complex trait. Molecular characterization of these genetic loci is of great interest for human clinical medicine.

Relevant Literature

The mouse tub mutation is described in Coleman and Eicher (1990) *J Hered* 81:424–7 as an autosomal recessive mutation located on chromosome 7, which causes slowly developing but ultimately severe obesity. Ohlemiller et al (1995) *Neuroreport* 6:845–9 and Heckenlively et al. (1995) *P.N.A.S.* 92:11100–11104 describe hearing loss and progressive retinal degeneration in tubby mice. The retinal degeneration is characterized by loss of photoreceptor cells, resulting in abnormal electroencephalograms by 3 weeks of age. Jones et al (1992) *Genomics* 14:197–9 localize the tub locus to a specific region of chromosome 7, and demonstrate that it is distinct from the insulin-2 locus. The cholecystokinin receptor gene is shown to tightly linked to the tub locus in Samuelson et al. (1995) *Genome* 6:242–6.

The positional cloning of the mouse ob gene is described in Zhang et al. (1994) *Nature* 372:425–432, and has the Genbank accession number U22421. The mouse agouti gene is described by Miller et al. (1993) *Genes Dev* 7:454–67. The db gene encodes the receptor for the ob gene product, as described in Lee et al. (1996) *Nature* 379:632–635.

Noben-Trauth et al. (1996) *Nature* 380:534–538 and Kleyn et al. (1996) *Cell* 65:281–290 describe the human and mouse genes associated with tubby. The carboxy terminal 260 amino acids of tubby show a strong similarity to a mouse testis-specific cDNA (GenBank accession number X69827).

SUMMARY OF THE INVENTION

A novel mammalian obesity associated locus is provided as an isolated cDNA, its corresponding genomic sequence, and a purified protein. The locus is also associated with a genetic predisposition to retinal and cochlear degeneration. The nucleic acid compositions find use in identifying homologous or related proteins and the DNA sequences encoding such proteins; in producing compositions that modulate the expression or function of the protein; and in studying associated physiological pathways. In addition, modulation of the gene activity in vivo is used for prophylactic and therapeutic purposes, such as treatment of obesity and retinal degeneration, identification of cell type based on expression, and the like. The DNA is further used as a diagnostic for genetic predisposition to obesity.

DESCRIPTION OF THE SPECIFIC EMBODIMENTS

Figure 1:
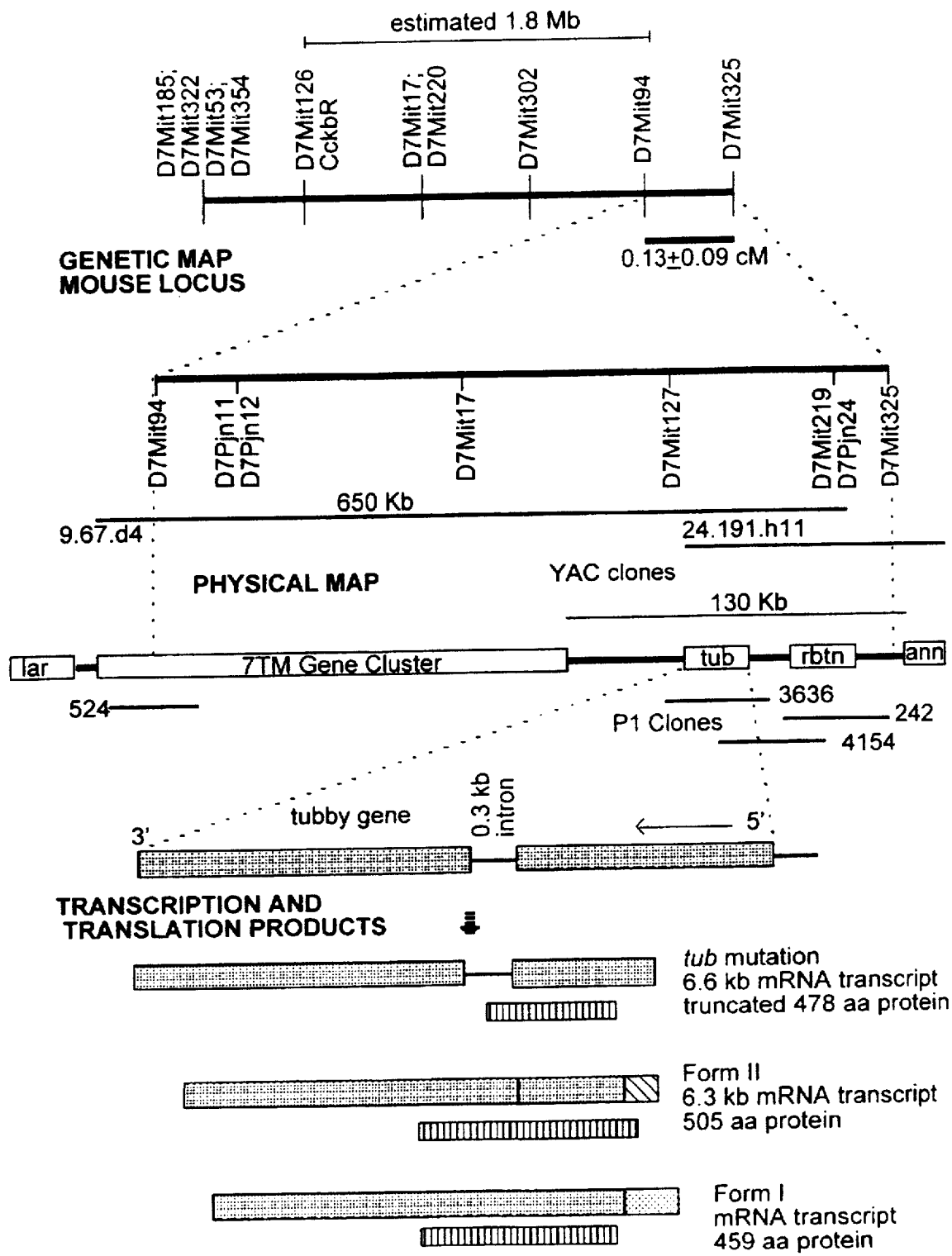
FIG. 1 shows the relationship of physical and genetic maps of the mouse tubby locus, and the transcriptional and translational products of the locus.

Mammalian genes associated with maturity-onset obesity are provided (tubby). Certain individuals having a genetic predisposition to obesity are shown to have a nucleotide sequence in the tubby gene that varies from the wild-type. This genetic variation is also associated with a predisposition to retinal and cochlear degeneration. The sequences of the subject human and mouse homologs are provided. Tubby nucleic acid compositions are used to identify homologous or related genes, to produce the corresponding protein, and in drug screening assays. The DNA is further used as a diagnostic for a specific genetic predisposition to late onset obesity, blindness and deafness.

As used herein, the term tubby designates a coding region, gene or gene product that maps to the chromosomal position of the tub mutation described by Coleman and Eicher, supra, and mammalian homologs thereof. The tub mutation confers a genetic predisposition to maturity onset obesity. Various clinical criteria are known in the art for defining morbid obesity in human populations, e.g. having a weight of about 20% above an individual's ideal body weight, etc. The data indicate that the tub mutation is also associated with adult-onset degeneration of the retina and cochlea. The cochlea of affected individuals shows pronounced degeneration of the organ of Corti and loss of afferent neurons in the base, with relative sparing of the apex.

The term tubby encompasses both the normal mammalian sequence and the mutated sequence responsible for the tub phenotype. The gene is expressed at high levels in brain, eye and testis, and at lower levels in various adult and fetal tissues, including small and large intestine, ovary and adipose tissue. Different transcriptional products are formed by alternative exon splicing in the 5' end of the gene, designated herein as Form I and Form II. Form II is the major expressed form in brain tissue.

The wild-type mouse and human tubby cDNA sequences (Form I) are shown in the Sequence Listing as SEQ ID NO:1 and SEQ ID NO:6, respectively. The predicted amino acid sequences for human and mouse are identified as SEQ ID NO:2 and SEQ ID NO:7, respectively. The Form I mouse cDNA encodes a protein of 459 amino acids. The mouse tubby cDNA sequence (Form II) is shown in the Sequence Listing as SEQ ID NO:3. The wild-type Form II mouse cDNA has a 1,584 bp open reading frame, encoding a 505 amino acid protein (SEQ ID NO:4). The human Form II cDNA (SEQ ID NO:26) has a 1,683 bp open reading frame, encoding a 561 amino acid protein (SEQ ID NO:27). The human Form II sequence provided herein differs from the sequence previously published by Kleyn et al. (1996) supra., in the sequence of the first 68 amino acids, which corresponds to two novel coding exons (SEQ ID NO:28, nt. 209 to 396; SEQ ID NO:28, nt. 1012 to 1419).

The mutation in tub/tub mice is a G to T transversion at position 1704 resulting in a splicing defect. The mutated gene sequence (starting at nt 1566 of SEQ ID NO:3) is shown in SEQ ID NO:5, and the predicted protein sequence, which is truncated from the wild-type sequence, is shown in SEQ ID NO:25 (starting from amino acid 453 of SEQ ID NO:4). FIG. 1 shows the different transcriptional and translational products of the tubby gene.

Identification of tubby homologs is based on similarity of sequence, chromosomal synteny, or both. The term homology is used to indicate a likeness of structure and conservation of biological function. Calculations of nucleic acid or amino acid sequence identity, as described below, provide a convenient method of identifying homologous or related genes, herein "homologs". Such homologs may be members of a gene family present in the same genome, or may be corresponding genes from different species. Chromosomal synteny may be used to further distinguish between homologous genes when there is sufficient evolutionary conservation between the genomes that are being compared, e.g. between mammalian species. A "syntenic homolog" has both sequence identity to the reference gene, and has the corresponding chromosomal location in relation to closely linked genes. As an example, the nucleic acid sequences of SEQ ID NO:1 and SEQ ID NO:6 are syntenic homologs. Syntenic homologs have a high probability of sharing spatial and temporal localization of gene expression, and of encoding proteins that fill equivalent biological roles.

The "tubby gene" shall be intended to mean the open reading frame encoding specific polypeptides, as well as adjacent 5' and 3' non-coding nucleotide sequences involved in the regulation of expression of the protein, and will include up to about the length of the mature mRNA. Typically an mRNA sequence will have a continuous open reading frame encoding the desired polypeptide.

The term "cDNA" as used herein is intended to include all nucleic acids that share the arrangement of sequence elements found in native mRNA species, where sequence elements may be exons, 3' and 5' non-coding regions and introns. Normally mRNA species have contiguous exons, with the intervening introns deleted. However, some mutations, e.g. tub, result in abberrant splicing and inclusion of intron sequence in the mature mRNA.

Under some conditions it has been found that a genomic sequence is preferable to a cDNA sequence for expression. In most mammalian genes the genomic sequence will have non-contiguous open reading frames, where introns interrupt the coding regions. A genomic sequence of interest comprises the nucleic acid present between the initiation codon and the stop codon, as defined in the listed sequences, including all of the introns that are normally present in a native chromosome. It may further include the 3' and 5' untranslated regions up to the length of the mature mRNA. It may further include specific transcriptional and translational regulatory sequences, such as promoters, enhancers, etc., up to about 1 kb of flanking genomic DNA at either the 5' or 3' end of the coding region.

A preferred genomic sequence will lack those sequences that are linked to tubby in a native chromosome but which do not contribute to the biological function of the tubby gene. Such sequences are conveniently identified through their relationship to polymorphic markers, as described in Dietrich et al. (1996) Nature 380:149 and Dib et al. (1996) Nature 380:152. The mouse genomic tubby sequence will typically lack the polymorphic markers D7Mit94, D7Mit17, and D7Mit325. The human tubby sequence will typically lack the polymorphic markers D11S909 and D11S1331.

The nucleic acid compositions of the subject invention encode all or a part of the subject polypeptides. Fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt, more usually at least about 35 nt. Such small DNA fragments are useful as primers for PCR, hybridization screening, etc. For use in amplification reactions, such as PCR, a pair of primers will be used. The exact composition of the primer sequences is not critical to the invention, but for most applications the primers will hybridize to the subject tubby sequence under stringent conditions. Conditions for stringent hybridization are known in the art, for example one may use a solution of 5× SSC and 50% formamide, incubated at 42° C. It is preferable to chose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The DNA sequences are obtained in substantial purity, generally as a sequence other than a sequence of an intact mammalian chromosome. Usually, the DNA will be obtained substantially free of other nucleic acid sequences that do not include an tubby sequence or fragment thereof, generally being at least about 50%, usually at least about 90% pure and are typically "recombinant", i.e. flanked by one or more nucleotides with which it is not normally associated on a naturally occurring chromosome.

The DNA sequences may be used in a variety of ways. They may be used as probes for identifying other tubby polypeptides, including homologs and syntenic homologs. Mammalian homologs have substantial sequence similarity to the subject sequences, i.e. at least 80%, preferably at least 90%, more preferably at least 95% sequence identity with the nucleotide sequence of the subject DNA sequence. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithims for sequence analysis are known in the art, and include BLAST, described in Altschul et al. (1990) *J Mol Biol* 215:403–10; ADVANCE and ADAM, described in Torelli and Robotti (1994) *Comput Appl Biosci* 10:3–5; and FASTA, described in Pearson and Lipman (1988) *P.N.A.S.* 85:2444–8.

The DNA sequences may be used in a variety of ways. They may be used as probes for identifying other tubby polypeptides, including novel subfamily members, homologs and syntenic homologs. Mammalian homologs have substantial sequence similarity to the subject sequences, i.e. at least 80%, preferably at least 90%, more preferably at least 95% sequence identity with the nucleotide sequence of the subject DNA sequence. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithims for sequence analysis are known in the art, such as BLAST, described in Altschul et al (1990) *J Mol Biol* 215:403–10.

Non-identical nucleic acids with sequence similarity are detected by hybridization under low stringency conditions, for example, at 50° C. and 10× SSC (0.9M saline/0.09M sodium citrate) and remain bound when subjected to washing at 55° C. in 1× SSC. By using probes, particularly labeled probes of DNA sequences, one can isolate homologous or related genes. The source of homologous genes may be any mammalian species, e.g. primate species, particularly human; murines, such as rats and mice, canines, felines, bovines, ovines, equines, etc.

For hybridization probes, it may be desirable to use nucleic acid analogs, in order to improve the stability and and binding affinity. A number of modifications have been described that alter the chemistry of the phosphodiester backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire phosphodiester backbone with a peptide linkage.

Sugar modifications are also used to enhance stability and affinity. The a-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

The DNA sequences, particularly nucleic acid analogs as described above, may be used as antisense sequences. The antisense sequences may be used by themselves or in conjunction with various toxic moieties, such as metal chelates, sensitizers, ribozymes, and the like. Antisense sequences may be used to study the effect of a loss of function.

The DNA may also be used to identify expression of the gene in a biological specimen. The manner in which one probes cells for the presence of particular nucleotide sequences, as genomic DNA or RNA, is well-established in the literature and does not require elaboration here. Conveniently, a biological specimen is used as a source of mRNA. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose and then probed with a fragment of the subject DNA as a probe. Other techniques may also find use. Detection of mRNA having the subject sequence is indicative of tubby gene expression in the sample.

The tubby nucleic acid sequence is used to diagnose a genetic predisposition to obesity, blindness or deafness by analysis of germline DNA for a predisposing mutation, where presence of the altered gene confers an increased susceptibility to one or more of these conditions. Predisposing mutations alter the normal function of tubby. Individuals are screened by analyzing their germline gene sequence for the presence of a predisposing mutation, as compared to a normal sequence. A "normal" sequence of tubby is provided in SEQ ID NO:1 and SEQ ID NO:3 (mouse), and SEQ ID NO:6 and SEQ ID NO:26 (human). The normal tubby sequence shall be understood to include sequence variants in non-coding regions that do not affect the level of expression of the gene, coding region variants that do not change the amino acid sequence, e.g. "third position" changes, and changes that result in an altered amino acid sequence but maintain substantially all of the normal protein function.

Predisposing mutations may occur in the control regions of the gene, where expression of the tubby gene is altered. Alternatively, the mutations will be found in the coding region of the gene, and will change the amino acid sequence of the protein, particularly the active site. Of particular interest are mutations in the splice donor or acceptor sites. In one embodiment of the invention, the predisposing mutation is at nucleotide 1704 of the tubby cDNA (SEQ ID NO:5), resulting in loss of a donor splice site.

The effect of a sequence variation on tubby gene expression or function is determined by kindred analysis for segregation of the sequence variation with the disease phenotype. The subject mutations generally have a recessive phenotype.

As an alternative to kindred studies, biochemical studies are performed to determine whether a candidate sequence variation in the tubby coding region or control regions affects the quantity or function of the protein. For example, a change in the promoter or enhancer sequence that downregulates expression of tubby may result in disease predisposition. Expression levels of a candidate variant allele are compared to expression levels of the normal allele by various methods known in the art. Methods for determining promoter or enhancer strength include quantitation of the expressed natural protein; insertion of the variant control element into a vector with a reporter gene such as β-galactosidase, chloramphenical acetyltransferase, etc. that provides for convenient quantitation; and the like.

A number of methods are used to determine the presence of a predisposing mutation in an individual. Genomic DNA is isolated from the individual or individuals that are to be tested. DNA can be isolated from any nucleated cellular source such as blood, hair shafts, saliva, mucous, biopsy, feces, etc. Methods using PCR amplification can be performed on the DNA from a single cell, although it is convenient to use at least about $10^5$ cells.

A number of methods are available for analyzing genomic DNA sequences. Where large amounts of DNA are available, the genomic DNA is used directly. Alternatively, the region of interest is cloned into a suitable vector and grown in sufficient quantity for analysis, or amplified by conventional techniques. Of particular interest is the use of the polymerase chain reaction (PCR) to amplify the DNA that lies between two specific primers. The use of the polymerase chain reaction is described in Saiki, et al. (1985) *Science* 239:487, and a review of current techniques may be found in Sambrook, et al. *Molecular Cloning: A Laboratory Manual, CSH Press* 1989, pp.14.2–14.33. Various methods are known in the art, and may be utilized for the subject screening, where oligonucleotide ligation is a means of detecting mutations, see Riley et al. (1990) *N. A. R.* 18:2887–2890; and Delahunty et al. (1996) *Am. J. Hum. Genet.* 58:1239–1246.

A detectable label may be included in the amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N', N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high afifnity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The amplified or cloned fragment may be sequenced by dideoxy or other methods, and the sequence of bases compared to the normal tubby sequence. Alternatively, where the predisposing mutation creates or destroys a recognition site for a restriction endonuclease, the fragment is digested with that endonuclease, and the products size fractionated to determine whether the fragment was digested. Fractionation is performed by gel electrophoresis, particularly acrylamide or agarose gels. Hybridization with the variant sequence may also be used to determine its presence, by Southern blots, dot blots, etc. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. The hybridization pattern of a control and variant sequence to an array of oligonucleotide probes immobilised on a solid support, as described in WO 95/11995, may also be used as a means of detecting the presence of variant sequences.

The subject nucleic acids can be used to generate transgenic animals or site specific gene modifications in cell lines. The modified cells or animals are useful in the study of tubby function and regulation. For example, a series of small deletions or substitutions may be made in the tubby gene to determine the role of different coding regions in obesity, signal transduction, substrate binding, etc.

DNA constructs for homologous recombination will comprise at least a portion of the tubby gene with the desired genetic modification, and will include regions of homology to the target locus. Conveniently, markers for positive and negative selection are included. Methods for generating cells having targeted gene modifications through homologous recombination are known in the art. For various techniques for transfecting mammalian cells, see Keown et al. (1990) Methods in Enzymology 185:527–537.

For embryonic stem (ES) cells, an ES cell line may be employed, or ES cells may be obtained freshly from a host, e.g. mouse, rat, guinea pig, etc. Such cells are grown on an appropriate fibroblast-feeder layer or grown in the presence of leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination. Those colonies that show homologous recombination may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected. The chimeric animals are screened for the presence of the modified tubby gene and males and females having the modification are mated to produce homozygous progeny. The transgenic animals may be any non-human mammal, such as laboratory animals, domestic animals, etc. The transgenic animals may be used to determine the effect of a candidate drug on obesity or retinal and cochlear degeneration in an in vivo environment.

Investigation of gene function may also utilize non-mammalian models, particularly using those organisms that are biologically and genetically well-characterized, such as *C. elegans, D. melanogaster* and *S. cerevisiae*. The subject gene sequences may be used to complement defined genetic lesions in order to determine the physiological and biochemical pathways involved in tubby function. A number of human genes have been shown to complement mutations in lower eukaryotes. Drug screening may be performed in combination with complementation studies. Many mammalian genes have homologs in yeast and lower animals. The study of such homologs' physiological role and interactions with other proteins can facilitate understanding of biological function. In addition to model systems based on genetic complementation, yeast has been shown to be a powerful tool for studying protein-protein interactions through the two hybrid system described in Chien et al. (1991) *P.N.A.S.* 88:9578–9582.

To produce tubby protein the DNA sequences are expressed by insertion into an appropriate expression vector, where the native transcriptional initiation region may be employed or an exogenous transcriptional initiation region, i.e. a promoter other than the promoter which is associated with the gene in the normally occurring chromosome. The promoter is operably linked to the coding sequence of the tubby gene to produce a translatable mRNA transcript. The promoter may be introduced by recombinant methods in vitro, or as the result of homologous integration of the sequence into a chromosome. A wide variety of constitutive or inducible promoters are known for a wide variety of expression hosts, where the expression hosts may be prokaryotes or eukaryotes, particularly *E. coli; B. subtilis*; yeast cells; mammalian cells; e.g. Cos cells. HeLa cells, L(tk-), primary cultures; insect cells; *Xenopus laevis oocytes*; and the like. Many strong promoters for mammalian cells are known in the art, including the β-actin promoter, SV40 early and late promoters, immunoglobulin promoter, human cytomegalovirus promoter, retroviral LTRs, etc.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the tubby gene or fragment thereof, and a transcriptional termination region. Of particular interest is the use of sequences that allow for the expression of functional epitopes or domains, usually at least about 24 nucleotides in length, more usually at least about 48 nucleotides in length, and up to the complete open reading frame of the gene. After introduction of the DNA, the cells containing the construct may be selected by means of a selectable marker, the cells expanded and then used for expression.

The expression cassettes may be introduced into a variety of vectors, e.g. plasmid, BAC, YAC, bacteriophage such as lambda, P1, M13, etc., animal or plant viruses, and the like, where the vectors are normally characterized by the ability to provide selection of cells comprising the expression vectors. The vectors may provide for extrachromosomal maintenance, particularly as plasmids or viruses, or for integration into the host chromosome. Where extrachromosomal maintenance is desired, an origin sequence is provided for the replication of the plasmid, which may be low- or high-copy copy number. A wide variety of markers are available for selection, particularly those which protect against toxins, more particularly against antibiotics. The particular marker that is chosen is selected in accordance with the nature of the host, where in some cases, complementation may be employed with auxotrophic hosts. Introduction of the DNA construct may use any convenient method, e.g. conjugation, bacterial transformation, calcium-precipitated DNA, electroporation, fusion, transfection, infection with viral vectors, biolistics, etc.

The DNA sequence may encode amino acid sequences that differ from the native sequence of a tubby polypeptide. The sequence may encode polypeptide analogs, fragments or derivatives of substantially similar polypeptides that differ from the naturally-occurring forms in terms of the identity of location of one or more amino acid residues (deletion analogs containing less than all of the residues specified for the protein, substitution analogs wherein one or more residues are replaced by other residues and addition analogs wherein one or more amino acid residues are added to a terminal or medial portion of the polypeptides) and which share some or all of the properties of naturally-occurring forms. Of particular interest are mutations that confer a genetic predisposition to obesity, and/or retinal and cochlear degeneration.

Sequence analogs include the incorporation of preferred codons for expression in non-mammalian host cells; the provision of sites for cleavage by restriction endonuclease enzymes; the addition of promoters operatively linked to enhance RNA transcription; and the provision of additional initial, terminal or intermediate DNA sequences that facilitate vector construction.

With the availability of the protein in large amounts by employing an expression host, the protein may be isolated and purified in accordance with conventional ways. A lysate may be prepared from the expression host and purified using HPLC, exclusion chromatography, gel electrophoresis, affinity chromatography, or other purification techniques as known in the art. The purified protein will generally be at least about 80% pure, preferably at least about 90% pure, and may be up to 100% pure. By pure is intended free of other proteins, as well as cellular debris.

The polypeptide may be used for the production of antibodies. Antibodies are prepared in accordance with conventional methods, where the expressed polypeptide or protein is used as an immunogen, by itself or conjugated to known immunogenic carriers, e.g. KLH, BSA, etc. Various adjuvants may be employed, as appropriate. For monoclonal antibodies, after one or more booster injections, the spleen of the immunized animal is isolated, the splenocytes immortalized, and then screened for high affinity antibody binding. The immortalized cells, i.e. hybridomas, producing the desired antibodies may then be expanded. For further description, see *Monoclonal Antibodies: A Laboratory Manual*, Harlow and Lane eds., Cold Spring Harbor Laboratories, Cold Spring Harbor, N.Y., 1988. The antibodies find use in diagnostic assays for detection of the presence of tubby in patient samples.

By providing for the production of large amounts of tubby protein, one can identify ligands or substrates that bind to, or modulate the action of tubby. The purified protein may be used for determination of three-dimensional crystal structure, which can be used for modeling intermolecular interactions. The subject polypeptides or functional domains thereof are used to screen for agonists or antagonists that modulate the interaction of tubby with its normal substrate, or proteins with which tubby interacts in a normal cell. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like.

The term "agent" as used herein describes any molecule, protein, or pharmaceutical with the capability of directly or indirectly altering the physiological function of tubby. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used.

The mixture of components are added in any order that provides for the requisite binding. Incubations are performed at any temperature that facilitates optimal activity, typically between 4° and 40° C. Incubation periods are selected for optimum activity, but may also be optimized to facilitate rapid high-throughput screening. Typically between 0.1 and 1 hours will be sufficient.

The compounds having the desired pharmacological activity may be administered in a physiologically acceptable carrier to a host for treatment of obesity, retinal degeneration or cochlear degeneration attributable to a defect in tubby function. The inhibitory agents may be administered in a variety of ways, orally, parenterally e.g. subcutaneously, intraperitoneally, intravascularly, etc. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

The present data indicate that the tubby protein is associated with degeneration of specific neurons in the retina, cochlea and pituitary/hypothalamus region. The histology is consistent with apoptosis of the affected neurons. The cluster of defects present in the tubby phenotype, i.e. adult onset obesity, blindness and deafness, may be accounted for by highly specific neuronal cell death that is triggered by either the expression of a mutated tubby gene product or by the lack of functional wild-type tubby protein. This is supported by an observation of specific hypothalamus and pituitary neuron death in several different strains of mice that are genetically predisposed to obesity. Increased body weight with age may therefore be a result of degeneration in brain areas regulating food intake and energy expenditure.

The availability of the subject gene sequences provides a means of analyzing the biology and biochemistry of obesity and specific neural degeneration through in vitro and in vivo drug screening, the use of transgenic animals, complementation of specific genetic lesions, etc., as previously described. A pathway of particular interest is apoptosis in neural cells.

Drug screening assays may be performed with mutant and wild-type tubby protein to detect agents that act as mimics, or agonists, or antagonists for tubby function. The interaction of tubby with other proteins in these pathways is of particular interest, and may be detected in a variety of assays, e.g. yeast two hybrid system, in vitro protein-protein binding assays, genetic complementation, etc. There are a number of characterized genes and gene products that operate to regulate or effect apoptosis.

Complementation in animal and yeast models is particularly useful in the study of apoptosis. The genetics of programmed cell death has been well-defined in several animal models. Both *C. elegans* and *D. melanogaster* regulate apoptosis through the expression of two gene products, ced-3 and ced-9, and rpr and hid, respectively. The relative simplicity of these pathways is attractive for biochemical and genetic analysis. Both animals are used as screening tools in conjunction with the subject gene sequences, and with their corresponding tubby homologs.

A number of apoptotic and anti-apoptotic genes are expressed in the brain, and may be involved in neural degeneration. Neurons depend on factors such as nerve growth factor and brain derived neurotrophic factor for survival, and may undergo apoptosis where the factor or its receptor are mutated. Among the anti-apoptotic genes of interest are bcl-2, bcl-xL and mcl-1. Inducers of apoptosis include fas (CD95), myc, bax, bcl-xs, TNF receptor and the family of cysteine proteases that includes interleukin 1 β-converting enzyme.

The following examples are offered by way of illustration and not by way of limitation.

EXAMPLE I

Identification of the Mouse Tubby Gene

The tubby mutation arose spontaneously in the C57BL/6J mouse strain. Homozygotes are recognizable by increased body weight at 3 to 4 months in males and at 4 to 6 months in females. Both sexes are fertile. The increased weight is composed of excess adipose tissue. Blood glucose is normal, but plasma insulin is increased prior to obvious signs of obesity and may rise to 20 times normal by 6 months. The islets of Langerhans are moderately enlarged with signs of hyperactivity and the mice display early onset retinal degeneration leading to blindness.

Materials and Methods

Genetic mapping of the tub locus. DNA samples isolated from the progeny of crosses between C57BL/6-tub/tub, CAST/Ei, AKR or NOD.NON-H2K$^b$ were genotyped for simple sequence length polymorphisms (Dietrich et al. (1994) *Nature Genet.* 7:220–245). All recombinants were progeny tested with a minimum of 20 offspring to confirm phenotypic classification. PCR amplification was performed as described in Naggert et al. (1995) *Nature Genet.* 10:135–141. The amplification primers used were as follows:

| Marker | Forward Primer | Reverse Primer |
| --- | --- | --- |
| D7Pjn11 | SEQ ID NO: 8 TTCACAAAAGCACACCTGG | SEQ ID NO: 9 GTCCCAAGGATGGAGACCT |
| D7Pjn12 | SEQ ID NO: 10 TGGTGAGCAAAACAAGGAAC | SEQ ID NO: 11 TGGGGAAAGCAATTTCTGG |
| D7Pjn24 | SEQ ID NO: 12 GCCTGTCAGCAAGGACCTT | SEQ ID NO: 13 CCATGTCCCAAACAAGATGG |

YAC clones were obtained by PCR screening of mouse YAC DNA pools from Research Genetics, Inc. (Huntsville, Ala.) and P1 clones were obtained from Genome Systems (St. Louis, Mo.). Briefly, DNA from YAC or P1 pools was used as a template in PCR with a specific primer pair as shown above. Only pools comprising a YAC or P1 that contains the sequence tag defined by the primer pair will yield an amplification product. Then the process is repeated with the subpools corresponding to the positive superpools. In the YACS this process is continued until a single positive YAC can be identified. In the case of P1s, no subpools for the secondary pools exist, so that the secondary pools are plated, transferred to nylon filter and screened with the labeled sequence tag obtained with the specific primer pair. A positive P1 pool is then isolated.

Additional P1 and cosmid clones were made from YAC967d4, which spans most of the minimal genetic interval, and were used in direct cDNA selection against cDNA from adult testis, brain and eye of C57BL/6 mice. Ten randomly chosen cosmids were used in the cDNA selection. P1s used include 3636, 1848, 2617, Y, 14.6, 4171, 17.12, 4154, and 24.2. cDNAs for selection were a mixture obtained from testis, brain and eye mRNA. The selection was carried out as described by Lovett, *Current protocols in Human Genetics* (eds. Dracopoli et al.) 6.3.1–13 (Current Protocols, N.Y. 1994) and modified by Segre et al. (1995) *Genomics* 28:549–559.

mRNA preparation. Whole organs from C57BL/6J and C57BL/6-tub/tub were flash frozen in liquid nitrogen, homogenized in 500 mM NaCl, 10 mM Tris pH 7.2, 10 mM EDTA, 2% SDS and incubated with 250 µg/ml proteinase K (EM Sciences, Gibbstown, N.J.) for 2 hours at 37° C. Oligo-dT cellulose (Pharmacia, Piscataway, N.J.) was added to the homogenate, placed on a shaking incubator for several hours and loaded onto PolyPrep chromatography column (BioRad, Richmond, Calif.). After washing in 100 mM NaCl, 10 mM Tris, pH 7.2, 0.1 mM EDTA, poly A$^+$ RNA was eluted in 10 mM Tris pH 7.2, 10 mM EDTA.

Northern blot analysis. 2–5 µg poly A$^+$ RNA was fractionated on a 1% agarose-formaldehyde gel, transferred to Hybond N+ membrane (Amersham) and hybridized with the indicated probes in the presence of 500 mM NaPO4, 7% SDS, 1 mM EDTA at 65° C. Blots were washed in 40 mM NaPO4, 1% SDS, 1 mM EDTA at 65° C., followed by a stringent wash in 0.1%SDS, 0.1× SSC at 68° C. Integrity, equal loading and transfer efficiency were assessed by control hybridization with a rat GAPDH probe.

An intron specific probe was generated by amplification of genomic PCR product of C13F2 and C13R with oligonucleotide primers C13F3 and C13R3. Nested PCR was used to generate the intron specific fragment in order to obtain a cleaner probe. Probe C15 was obtained by EcoRI digestion of the cDNA clone c15 from the cDNA selection. Probes were random labeled with 32P[αdCTP] (Amersham, Arlington Heights, Ill.). Genomic DNA was PCR amplified with oligonucleotide primers flanking the donor splice site, C13F2 and C13R, and was gel purified and manually sequenced by dideoxy cycle sequencing (Sequitherm, Epicentre Technologies, Madison, Wis.). Primer 2.61 F1 was used with C13R to obtain a probe DNA fragment for northern blots by amplifying cDNA. Probes were generated by random hexamer priming, as described by Sambrook et al., supra.

| Primers | |
| --- | --- |
| 2.61F | [SEQ ID NO: 14] ACCTGAGGCAGCAGAAGCT |
| C13R | [SEQ ID NO: 15] CAGCCAGTCTCTGGTTGGT |
| C13F2 | [SEQ ID NO: 16] TGCAGAACAAGACGCCAGT |
| C13F3 | [SEQ ID NO: 17] GATGTTGTACGCATGGTGC |
| C13R3 | [SEQ ID NO: 18] TGGAGACAGGGAGACCAGG |

Reverse transcription-PCR. RT-PCR was performed with RNA from adult tissues using primers 2.40R and 2.40F (specific to nucleotides 1080 and to 1423) or GAPDH. The tub gene specific primers span two introns with a combined length of about 1 kb. Two µg poly A+ RNA were treated with DNAse I (Boehringer Mannheim, Indianapolis, Ind.) and reverse transcribed using Superscript™ Preamplification System (Gibco/BRL, Gaithersburg, Md.). PCR was performed using 1–10 ng sscDNA, primer 2.40F [SEQ ID NO:19] GATGGCAAGAAGGTGTTCC and 2.40R [SEQ ID NO:20] TCATTGCGGGGGCGGATAC and Ampli-Taq™ (Perkin Elmer, Calif.) under the following conditions: 95° C. 1 min denaturation, 94° C. 20 sec, 58° C. 20 sec, 72° C. 30 sec for 49 cycles followed by 72° C. 2 min. Forward and reverse GAPDH oligomers were [SEQ ID NO:21] ATGGTGAAGGTCGGTGTGAA and [SEQ ID NO:22] ACCAGTAGACTCCACGACAT, respectively. The amplification products were electrophoresed in 1% agarose gel, transferred to Hybond N+ (Amersham) and hybridized with either exon or GAPDH cDNA probes.

cDNA library screening. A mouse testis cDNA library from mouse strain CD-1 (Stratagene, La Jolla, Calif.) inserted into lambda UNI-ZAP XR was screened according to the manufacturer's instructions with the 1.6 kb 2.61 F-C13R PCR probe, identifying 24 plaques, two of which were purified and sequenced automatically (Prism, Applied Biosystems, Foster City, Calif.). Clone length was between 1 and 2.5 kb. The coding region cDNA sequence of Form I is described in the sequence listing, SEQ ID NO:1. The predicted amino acid sequence is SEQ ID NO:2. The coding region cDNA sequence of Form II is described in the sequence listing SEQ ID NO:3, the predicted amino acid sequence is SEQ ID NO:4.

Results

Genetic Mapping. Tubby was previously mapped in an interspecific (CS1 BL/6-tub/tub X CAST/Ei)F$_1$ intercross to 2.4±1.4 cM from Hbb. Markers across a 20 cM interval encompassing Hbb were tested to identify areas of recombination and to define more closely the minimal tub region, using the DNA from the cross described above. Three mapping crosses were used to refine the minimal region containing the gene to between markers D7Mit94 and D7Mit325. FIG. 1 shows genetic and physical maps of the mouse tub region.

A total of 1468 meioses were tested in mapping outcrosses with CAST/Ei. 60 microsatellite markers were used, 91% of which were polymorphic between B6 and CAST. The minimal region containing tub identified by the CAST/Ei outcrosses was between markers D7Mit124 and D7Mit328 with a genetic distance of 0.27±0.14 cM.

In the NOD.NON-H2K$^b$ intercross with C57BL/6 tub/tub, 820 mice or 1640 meioses were tested. Initially, 680 meioses were tested proximally with D7Mit185 and distally with D7Mit130. As a narrower region was identified, 458 and 502 meioses were tested with proximal markers, D7Mit126 and D7Pjn2, respectively. Of 44 markers contained within the largest interval tested, 34 (77%) were polymorphic between C57BL-tub/tub and NOD.NON-H2K$^b$. Overall, 20 recombinant mice were identified in this intercross. The minimal region containing tub lay between markers D7Mit219 and D7Mit130 with a genetic distance of 0.18±0.11 cM.

775 F$_2$ progeny, or 1550 meioses, were tested with D7Mit126 and D7Mit130 as the flanking markers in the (C57BL/6-tub/tub X AKR)F$_1$ intercross. Only nine of the 34 markers mapping to this region were polymorphic between these parentals. The minimal genetic interval containing tub, between D7Pjn12 and D7Mit328, corresponds to a distance of 0.19±0.11 cM.

Physical Mapping. A YAC contig was established spanning the minimal genetic region, establishing order and distance for those markers not separated by recombinants. The minimal genetic interval was shown to be flanked by crossovers at D7Mit94 and D7Mit325, which could be mapped within P1 clones 524 and 242, respectively. The location of the tub gene relative to each crossover was unambiguously determined by progeny testing. Animals carrying crossovers in the region were mated to tub/tub homozygotes and the progeny examined for the tubby phenotype (50% tubby if the crossover chromosome still contained the tubby gene, 0% tubby if the crossover chromosome had lost the tubby gene).

Both flanking markers were shown to map within YAC67d4, giving a maximal physical separation of 650 kb. A high resolution physical map of the region was constructed by P1, BAC and cosmid assembly using STSs derived from end sequencing P1s, by subcloning and sequencing cosmid pools derived from YAC 132b11 (1 Mb, non-chimaeric) and by searching public databases.

Selected 0.6–1.5 kb cDNA clones were sequenced and analyzed for similarities to known sequences in GenBank using the BLASTN program (described in Altshul et al. (1990) *J. Mol. Bio.* 215:403–410), and for overlaps using the AssemblyLIGN program (Kodak, N.Y.). Unique cDNA clones and single clones from groups of overlapping clones were hybridized to Southern blots of EcoRI digested P1 DNA. Positive clones that mapped to the minimal region were analyzed for genomic alterations and aberrant expression between C57BL/6 and C57BL/6-tub/tub mice by Southern and northern blot analysis.

One cDNA clone, c33, from a DNA contig of 12 overlapping sequences, showed an altered hybridization pattern in tubby derived mRNA when compared to C57BL/6. Tubby mice express a slightly larger transcript in brain and testis, 6.6 kb vs. 6.3 kb. Furthermore, clone c33 identified a 2.1 kb transcript in tubby derived mRNA that is not observed in C57BL/6.

To determine the molecular basis of these differences, oligonucleotide primers were made according to the cDNA sequences from the contig of overlapping clones and used to PCR amplify gene specific fragments from cDNA and genomic DNA. Several oligonucleotide combinations derived from the carboxyterminal portion of the gene, as described above, generated an amplification product from tubby derived cDNA that was 300 bp longer than from C57BL/6 cDNA. The genomic nucleotide sequence was compared, and it was found that there was a G to T transversion in the tubby donor splice site, changing the wild-type donor splice site consensus sequence from GTGAGT to TTGAGT. To confirm that the larger transcript observed in tub was due to the presence of this unspliced carboxy terminal intron, a PCR generated probe specific for the intron was hybridized to a northern blot. The probe detected a transcript only in the tubby mRNA, but not in wild-type. Comparison of the sequence surrounding this donor splice site in standard inbred strain from historically independent lineages, AKR/J, BALB/cJ, DBA/2J, two wild-derived strains, CZECHII/Ei and SKIVE/Ei, as well as from rabbit and rat, showed conservation of the C57BL/6 sequence, suggesting that the nucleotide change is not a normal allelic form, but a mutation leading to the abnormal transcripts. The 2.1 kb transcript is likely to arise from truncation of the full length transcript by introduction of a polyadenylation site contained in the unspliced intron. This is supported by hybridization analysis with a sequence 3' of the unspliced intron, which does not hybridize to the 2.1 kb transcript.

Northern blot analysis of adult tissues shows strong expression of tubby in brain, eye and testis. Using a more sensitive RT-PCR assay, gene expression was also detected in the small and large intestine, ovary and adipose tissue of adult mice.

To assemble a full-length cDNA, 24 clones were isolated from a mouse testis oligo-dT primed cDNA library (Stratagene, La Jolla, Calif.). Two forms were identified. The sequence of Form I (SEQ ID NO:1) from nt 393–2579 is identical to Form II (SEQ ID NO:3) from nt 248–2434. The 5' end of the coding regions differ, resulting in a Form I protein that is 46 amino acids shorter than Form II.

The predominantly hydrophilic nature of the predicted amino acid sequence, and absence of a signal sequence, suggest a cytosolic localization for the protein. The carboxy terminal 260 amino acids show a strong similarity (62% identity) to a putative mouse testis-specific phosphodiesterase (GenBank accession number X69827), as well as the C. elegans 48.2K protein (GenBank Q09306, 59% identity). The aminoterminal portion of the tubby gene shows no similarity to any known protein in database searches (BLASTP).

EXAMPLE II

Characterization of the Human Tubby Gene

The human tubby gene was isolated from a human cDNA library by the following methods.

A cDNA library generated from human brain mRNA and cloned into lambda gt11 (Clontech, Palo Alto, Calif.) was used to isolate the human tubby gene. The phage library was plated at $1.2 \times 10^6$ pfu/plate onto *E. coli* Y1090 in standard bacterial medium. The plates were incubated for 9 hours at 37° C. Two nitrocellulose filters were lifted from each plate as described in Sambrook et al., supra., pp.2.114. The filters were hybridized in 10% dextran sulfate, 1% SDS, 1M NaCl, 100 µg/ml salmon testes DNA and the $^{32}$P labeled probes described below, at 65° C. for 16 hr.

The hybridization probes are PCR amplification products of cDNA sequences isolated by exon trapping with the P1 clone 3636, as described in Example 1. The cDNA sequences were cloned into the pSPL3b vector (BRL, Bethesda, Md.) and amplified according to the manufacturer's instrictions. A 171 bp probe was generated having the sequence of SEQ ID NO:23, and a 99 bp probe was generated having the sequence of SEQ ID NO:24. The DNA was labeled by random hexamer priming, as described in Example 1.

After hybridization, the filters were washed at 65° C. in a buffer of 2× SSC, 0.1% SDS for 45 min, followed by two washes in 0.2× SSC, 0.1% SDS for 45 minutes each. Positive plaques were isolated and rescreened. A total of 18 positive plaques were identified.

The cDNA inserts from the positive plaques were amplified by PCR and subcloned. Briefly, agar plugs containing positive phage plaques were picked, and resuspended in 10 mM Tris, 1 mM EDTA to elute phage. A PCR reaction was set up with phage eluate and primers specific for the region of lambda gt11 flanking the insert. The individual amplification products were digested with EcoRI, purified by gel electrophoresis and QIAEX II™ gel extraction kit (Qiagen), and inserted into pUC9 at the EcoRI site. The subcloned inserts ranged in size from 1.0–3.3 kb.

Nine of the plasmids were purified using a QIAGEN™ plasmid kit according to the manufacturer's instructions, and sequenced automatically (Prism, Applied Biosystems, Foster City, Calif.). The sequences were assembled, edited and analyzed using a suite of programs, including the BLASTN program (described in Altshul et al. (1990) *J. Mol. Bio.* 215:403–410), and for overlaps using the AssemblyLIGN program (Kodak, N.Y.). The human Form I cDNA sequence is shown in SEQ ID NO:6. The predicted amino acid sequence is shown in SEQ ID NO:7. The human Form II cDNA is shown in SEQ ID NO:26. The predicted amino acid sequence is shown in SEQ ID NO:27. Form II is 101 amino acids longer at the amino terminus than Form I, but is otherwise identical.

A confirmation of the 5' end sequence for the human Form II cDNA was obtained by sequencing genomic clones. A BAC containing the human tubby genomic region was identified from a human genomic BAC library (Research Genetics). BAC clones were pooled, and the DNA screened for the presence of tubby sequences by PCR amplification with primers specific to the 3' untranslated region.

The genomic region that contains the human Form II 5' end sequence is shown in SEQ ID NO:28. The two coding exons have the sequence shown in (SEQ ID NO:28, nt. 209 to 396; and SEQ ID NO:28, nt. 1012 to 1419).

Table of Sequences

| Sequence | Molecule | SEQ ID NO |
|---|---|---|
| Mouse Form I cDNA | dsDNA | 1 |
| translation of above | amino acid | 2 |
| Mouse Form II cDNA | dsDNA | 3 |
| translation of above | amino acid | 4 |
| tub mutation | dsDNA | 5 |
| Human Form I cDNA | dsDNA | 6 |
| translation of above | amino acid | 7 |
| D7Pjn11 | primer | 8 |
| D7Pjn11 | primer | 9 |
| D7Pjn12 | primer | 10 |
| D7Pjn12 | primer | 11 |
| D7Pjn24 | primer | 12 |
| D7Pjn24 | primer | 13 |
| 2.61F | primer | 14 |
| C13R | primer | 15 |
| C13F2 | primer | 16 |
| C13F3 | primer | 17 |
| C13R3 | primer | 18 |
| 2.40F | primer | 19 |
| 2.40R | primer | 20 |
| GAPDH | primer | 21 |
| GAPDH | primer | 22 |
| ET_3636.p01.a04 | probe | 23 |
| ET_3636.p01.d01 | probe | 24 |
| tub translation | amino acid | 25 |
| Human Form II cDNA | dsDNA | 26 |
| translation of above | amino acid | 27 |
| Human 5' genomic sequence | dsDNA | 28 |

It is evident from the above results that a novel gene associated with mammalian obesity has been identified and characterized in mice and humans. A splicing defect in the gene leads to retinal and cochlear degeneration, as well as maturity onset-obesity. These genes and gene products find use in diagnosis, therapy, and drug identification.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated nucleic acid molecule comprising a sequence encoding a mammalian tubby protein consisting of the amino acid sequence of SEQ ID NO:27.

2. An isolated nucleic acid molecule comprising the nucleotide sequence of SEQ ID NO:26.

3. An isolated cell transfected with the nucleic acid molecule according to claim 1.

4. A hybridization probe consisting of at least 18 contiguous nucleotides of SEQ ID NO:28, nucleotides 209–396.

* * * * *